US012589068B2

(12) United States Patent
Taylor et al.

(10) Patent No.: US 12,589,068 B2
(45) Date of Patent: Mar. 31, 2026

(54) CONTRACEPTIVE MEDICAL DEVICES

(71) Applicant: POLY-MED, INC., Anderson, SC (US)

(72) Inventors: Michael Scott Taylor, Anderson, SC (US); Brian Gaerke, Travelers Rest, SC (US); David Gravett, Mountain View, CA (US); Anna Paola Soliani, Anderson, SC (US); Kyle Garcia, Anderson, SC (US)

(73) Assignee: POLY-MED, INC., Anderson, SC (US)

( * ) Notice: Subject to any disclaimer, the term of this patent is extended or adjusted under 35 U.S.C. 154(b) by 791 days.

(21) Appl. No.: 17/774,784

(22) PCT Filed: Nov. 11, 2020

(86) PCT No.: PCT/US2020/059968
§ 371 (c)(1),
(2) Date: May 5, 2022

(87) PCT Pub. No.: WO2021/096926
PCT Pub. Date: May 20, 2021

(65) Prior Publication Data
US 2022/0395456 A1 Dec. 15, 2022

Related U.S. Application Data

(60) Provisional application No. 63/019,884, filed on May 4, 2020, provisional application No. 62/934,090, filed on Nov. 12, 2019.

(51) Int. Cl.
*A61K 9/00* (2006.01)
*A61F 6/08* (2006.01)
(Continued)

(52) U.S. Cl.
CPC .............. *A61K 9/0036* (2013.01); *A61F 6/08* (2013.01); *A61K 33/26* (2013.01); *A61K 47/32* (2013.01);
(Continued)

(58) Field of Classification Search
CPC ............ A61F 6/06; A61F 6/08; A61K 9/0036
See application file for complete search history.

(56) References Cited

U.S. PATENT DOCUMENTS 3,545,439 A    12/1970   Duncan
3,920,805 A    11/1975   Roseman
(Continued)

FOREIGN PATENT DOCUMENTS

CN         101442984 A       5/2009
CN         102600001 A       7/2012
(Continued)

OTHER PUBLICATIONS

Garlotta, A literature review of poly(lactic acid), Journal of polymers and the environment, 2001, 9(2), 63-84.
(Continued)

*Primary Examiner* — Keri J Nelson
(74) *Attorney, Agent, or Firm* — Meunier Carlin & Curfman LLC

(57) ABSTRACT

Disclosed herein are contraceptive medical devices that include at least a polymeric ring, a porous barrier material and an injection molding guide, where the guide may be symmetrical and/or have one or a plurality of planar surfaces, where the device may optionally administer at least one active agent.

15 Claims, 4 Drawing Sheets

(51) Int. Cl.

| | |
|---|---|
| *A61K 33/26* | (2006.01) |
| *A61K 47/32* | (2006.01) |
| *B29B 11/08* | (2006.01) |
| *B29C 45/14* | (2006.01) |
| *B33Y 80/00* | (2015.01) |
| *B29K 21/00* | (2006.01) |
| *B29L 31/00* | (2006.01) |

(52) U.S. Cl.

CPC ........ *B29B 11/08* (2013.01); *B29C 45/14065* (2013.01); *B33Y 80/00* (2014.12); *B29C 2045/14131* (2013.01); *B29K 2021/00* (2013.01); *B29K 2995/006* (2013.01); *B29L 2031/753* (2013.01)

(56) References Cited

U.S. PATENT DOCUMENTS

| | | | |
|---|---|---|---|
| 3,995,634 | A | 12/1976 | Drobish |
| 4,012,496 | A | 3/1977 | Schopflin et al. |
| 4,200,090 | A | 4/1980 | Drobish |
| 4,629,449 | A | 12/1986 | Wong |
| 4,822,616 | A * | 4/1989 | Zimmermann .......... A61F 6/08 |
| | | | 424/432 |
| 4,883,071 | A | 11/1989 | Pickhard et al. |
| 5,211,952 | A | 5/1993 | Spicer |
| 5,624,704 | A | 4/1997 | Darouiche |
| 5,681,568 | A | 10/1997 | Goldin |
| 5,928,666 | A | 7/1999 | Farinas et al. |
| 6,083,916 | A | 7/2000 | Nonomura et al. |
| 6,159,240 | A | 12/2000 | Sparer et al. |
| 6,235,313 | B1 | 5/2001 | Mathiowitz et al. |
| 6,309,669 | B1 | 10/2001 | Setterstrom et al. |
| 6,413,539 | B1 | 7/2002 | Shalaby |
| 6,416,779 | B1 | 7/2002 | D'Augustine et al. |
| 6,462,169 | B1 | 10/2002 | Shalaby |
| 6,572,874 | B1 | 6/2003 | Harrison et al. |
| 6,794,485 | B2 | 9/2004 | Shalaby et al. |
| 6,939,569 | B1 | 9/2005 | Green et al. |
| 6,951,654 | B2 | 10/2005 | Malcolm et al. |
| 7,048,753 | B2 | 5/2006 | Shalaby |
| 7,070,858 | B2 | 7/2006 | Shalaby et al. |
| 7,192,437 | B2 | 3/2007 | Shalaby |
| 7,521,064 | B2 | 4/2009 | Saxena et al. |
| 7,910,126 | B2 | 3/2011 | Ahmed et al. |
| 8,057,817 | B2 | 11/2011 | Shalaby |
| 8,137,327 | B2 | 3/2012 | Sokal et al. |
| 8,323,679 | B2 | 12/2012 | Ahmed et al. |
| 8,399,013 | B2 | 3/2013 | Shalaby |
| 8,506,988 | B2 | 8/2013 | Shalaby et al. |
| 8,580,293 | B2 | 11/2013 | Ahmed et al. |
| 8,580,294 | B2 | 11/2013 | Malcolm et al. |
| 8,992,968 | B2 | 3/2015 | Shalaby |
| 9,006,278 | B2 | 4/2015 | Shalaby et al. |
| 9,034,365 | B2 | 5/2015 | Shalaby et al. |
| 9,566,267 | B2 | 2/2017 | Shalaby et al. |
| 2003/0059456 | A1 | 3/2003 | Malcolm et al. |
| 2004/0013730 | A1 | 1/2004 | Saxena et al. |
| 2004/0077601 | A1 | 4/2004 | Adams et al. |
| 2004/0260386 | A1 | 12/2004 | Shalaby |
| 2004/0265355 | A1 | 12/2004 | Shalaby |

| | | | |
|---|---|---|---|
| 2005/0053639 | A1 | 3/2005 | Shalaby |
| 2005/0175665 | A1 | 8/2005 | Hunter et al. |
| 2006/0195142 | A1 | 8/2006 | Shalaby |
| 2006/0240071 | A1 | 10/2006 | Lerner et al. |
| 2007/0243229 | A1 | 10/2007 | Smith et al. |
| 2007/0275034 | A1 | 11/2007 | Shalaby et al. |
| 2008/0069850 | A1 | 3/2008 | Shalaby et al. |
| 2009/0246254 | A1 | 10/2009 | Saxena et al. |
| 2009/0291925 | A1 | 11/2009 | Shalaby |
| 2010/0062039 | A1 | 3/2010 | Shalaby |
| 2010/0280464 | A1 | 11/2010 | De Graaff et al. |
| 2011/0056501 | A1 | 3/2011 | Kortesuo et al. |
| 2012/0053534 | A1 | 3/2012 | Mahashabde et al. |
| 2012/0097171 | A1 | 4/2012 | Pope |
| 2012/0177716 | A1 | 7/2012 | Ho et al. |
| 2013/0042873 | A1 | 2/2013 | Bechgaard et al. |
| 2015/0283160 | A1 | 10/2015 | Shalaby et al. |
| 2017/0020718 | A1 | 1/2017 | Gray et al. |
| 2019/0091141 | A1 | 3/2019 | Benhabbour et al. |

FOREIGN PATENT DOCUMENTS

| | | |
|---|---|---|
| CN | 103341175 A | 10/2013 |
| GB | 2475644 A | 5/2011 |
| WO | 1998004220 A1 | 2/1998 |
| WO | 2000059559 A1 | 10/2000 |
| WO | 2002015832 A1 | 2/2002 |
| WO | 2006010097 A2 | 1/2006 |
| WO | 2006065873 A2 | 6/2006 |
| WO | 2008007046 A1 | 1/2008 |
| WO | 2009048594 A2 | 4/2009 |
| WO | 2011005839 A1 | 1/2011 |
| WO | 2011016881 A2 | 2/2011 |
| WO | 2013013172 A1 | 1/2013 |
| WO | 2015153817 A1 | 10/2015 |
| WO | 2016156403 A1 | 10/2016 |
| WO | 2018215772 A1 | 11/2018 |

OTHER PUBLICATIONS

Malcolm et al. "Long-term, controlled release of the HIV microbicide TMC 120 from silicone elastomer vaginal rings," J Antimicrobial Chemotherapy, 2005, 56, 954-956.

Marques et al. Simulated Biological Fluids with Possible Application in Dissolution Testing, Dissolution Technologies, 2011, 18(3), 15-28.

Sheehan et al. Current and Emerging Azole Antifungal agents, Clinical Microbiology Reviews, 1999, 12, 40-79.

Shivhare et al. "Long acting intravaginal ring as a novel approach for antibacterial drug delivery," PHARMANEST—An International Journal of Advances in Pharmaceutical Sciences, 2013, 4(5), 888-901.

Woolfson et al. "Intravaginal ring delivery of the reverse transcriptase inhibitor TMC 120 as an HIV microbicide," Int. J. Pharm. 2006, 325, 82-89.

International Search Report and Written Opinion dated Mar. 25, 2021, for Application No. PCT/US2020/059968.

'Spermicide' (Hirsch), Aug. 1, 2019, online, retrieved from URL: https://web.archive.org.web.20190801005555/https://kidshealth.org./en/teens/contraception-spermicide.html.

\* cited by examiner

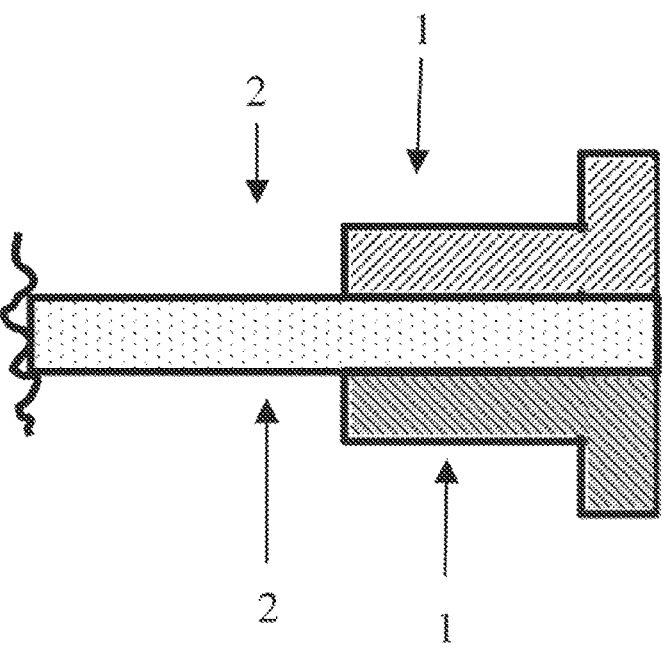
*FIG. 4*
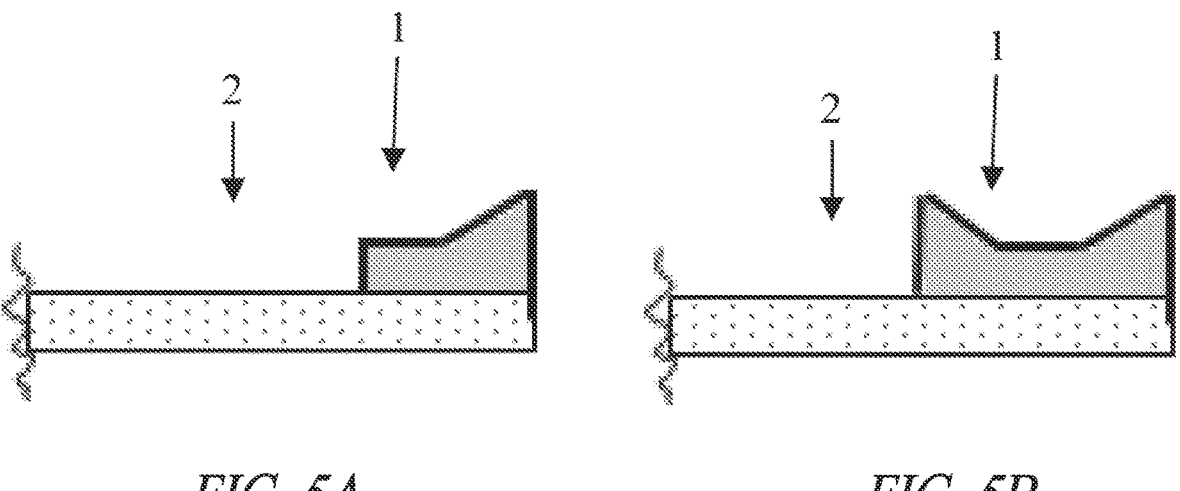
*FIG. 5A*            *FIG. 5B*

CONTRACEPTIVE MEDICAL DEVICES

CROSS-REFERENCE TO RELATED APPLICATION

This application is a national phase application under 35 U.S.C. § 371 of International Application No. PCT/US2020/059968, filed Nov. 11, 2020, which claims the benefit under 35 U.S.C. § 119 (e) of U.S. Provisional Patent Application No. 62/934,090, filed Nov. 12, 2019, and U.S. Provisional Application No. 63/019,884, filed May 4, 2022, which each application is herein incorporated by reference in its entirety for all purposes.

TECHNICAL FIELD

The present disclosure relates to medical devices for contraception, particularly disclosing an intravaginal medical device comprising a ring, an injection molding guide and a barrier material.

BACKGROUND

Effective contraceptive medical devices or pharmaceuticals are desired by fertile humans worldwide. The success rate of a contraceptive medical device depends not only upon the efficacy of a contraceptive method, but also upon a user's preference, the reversibility of the method's medical device or pharmaceutical; convenience for the user, and compliance by the user. The need for effective contraceptive methods, including pharmaceutical or medical devices, continues to be a critical need. It is estimated that fifty percent of pregnancies are unintended, and worldwide, a woman dies every two minutes from pregnancy and childbirth related issues.

Hormone-based pharmaceutical contraceptives have been used widely, but are now known to affect users systemically, and are contraindicated for individuals with a variety of cardiovascular conditions. Therefore, it, is desirable to provide new and improved contraceptive medical devices that provide localized administration of active agents, and that are easier to use than are conventional devices and methods. Accordingly, there is a need to provide local administration of one or more active agents, biocompatible, non-invasive, cost-effective, reversible and convenient contraceptive medical devices to prevent pregnancy. The present disclosure provides contraceptive medical devices and related devices and methods to meet this need.

SUMMARY

Briefly stated, the present disclosure provides contraceptive medical devices, components thereof, methods of making and using the contraceptive devices and components thereof, and compositions contained therein. In one aspect, the present disclosure provides a contraceptive device comprising a porous barrier material and an injection molding guide, the injection molding guide optionally affixed to the barrier material. The injection molding guide and the porous barrier material may each be at least partially encased within a polymeric ring that encircles the porous barrier material, and in one embodiment the injection molding guide is completely encased within the polymeric ring and the porous barrier material is partially encased within the polymeric ring. Thus, in one aspect the present disclosure provides a contraceptive device comprising a porous barrier material, an injection molding guide, and a polymeric ring, where the injection molding guide is entirely encased within the polymeric ring and the porous barrier material is partially encased within the polymeric ring. The injection molding guide may have symmetry so that two or more pins may equally engage with the injection molding guide during an injection molding process. The injection molding guide may have a plurality of planar surfaces, e.g., 3, or 4, or 5, or 6, or 7, or 8 planar surfaces. The injection molding guide is at least partially encased within a polymeric ring structure, and in one embodiment the injection molding guide is encased within the polymeric ring structure. For example, the present disclosure provides a contraceptive device comprising a polymeric ring, a porous barrier material and an injection molding guide, the injection molding guide comprising a plurality of planar surfaces, each of the injection molding guide and the porous barrier material at least partially embedded within the polymeric ring, where optionally the injection molding guide is completely embedded within the polymeric ring and the porous barrier material is partially embedded within the polymeric ring. As another example, the present disclosure provides a contraceptive device comprising a polymeric ring, a porous barrier material and an injection molding guide, the injection molding guide having a symmetrical appearance when viewed in cross-section, such that the left side of the cross sectional view is the mirror image of the right side of the cross sectional view, each of the injection molding guide and the porous barrier material at least partially embedded within the polymeric ring, where optionally the injection molding guide is completely embedded within the polymeric ring and the porous barrier material is partially embedded within the polymeric ring.

Optionally, the contraceptive device may be further characterized by features disclosed herein, e.g., it may be further characterized by one or more of the following features: the barrier material is a mesh; the barrier material is a fibrous mesh; the barrier material is fibrous; the barrier material is circular; the barrier material is substantially circular; the barrier material has a diameter, e.g., a diameter of about 40 mm to about 60 mm, for example, about 45 mm to about 53 mm; the injection molding guide is non-fibrous; the injection molding guide has a melting point above the temperature used for injection molding, e.g., above 120° C.; the injection molding guide has a uniform cross-section at all locations around the injection molding guide; the injection molding guide has a corner formed by two planar surfaces intersecting at an angle, optionally an angle between 45 degrees and 135 degrees, e.g., of 85-95 degrees, e.g., a 90 degree angle; the injection molding guide has a polymeric coating; the injection molding guide is uncoated; the injection molding guide does not contain a sizing polymer; the injection molding guide has a single composition throughout the support ring; the injection molding guide is biodegradable; the injection molding guide is located along an edge of the barrier material; the injection molding guide is located close to an edge of the barrier material; the injection molding guide extends into the porous barrier material; the injection molding guide is 3D-printed on the barrier material; the injection molding guide is injection molded onto the barrier material; the ring structure comprises an elastomeric polymer, e.g., a siloxane; the contraceptive device includes a biologically active agent located within the polymeric ring structure; the contraceptive device includes a ferrous compound located within the polymeric ring structure; the contraceptive device includes ferrous gluconate or a hydrate thereof located within the polymeric ring structure; the contraceptive device includes a ferrous compound and ascorbic acid, each located within the polymeric ring structure. These and other features and options for the contraceptive device of the present disclosure are described herein.

In one aspect, the present disclosure provides a kit comprising a contraceptive device as described herein, e.g., as described above, the kit further comprising at least one of a lubricant, a spermicidal gel, a spermicidal film, a contraceptive gel and an applicator.

In one aspect, the present disclosure provides a construct that can be used to form a contraceptive device of the present disclosure. The construct comprises a porous barrier material affixed to an injection molding guide, where the injection molding guide has a plurality of planar surfaces. Optionally, the construct may be further characterized by a feature described herein, e.g., one or more of the following features: the barrier material is a mesh; the barrier material is a fibrous mesh; the barrier material is fibrous; the barrier material is circular; the barrier material is substantially circular; the barrier material has a diameter of about 40 mm to about 60 mm, e.g., about 45 mm to about 53 mm; the injection molding guide is non-fibrous; the injection molding guide has a melting point above the temperature used for injection molding, e.g., above 120° C.; the injection molding guide has a uniform cross-section at all locations around the injection molding guide; the injection molding guide has a corner formed by two planar surfaces intersecting at an angle, such as an angle of about 45 degrees to about 135 degrees, such as 85-95 degrees, e.g., a 90 degree angle; the injection molding guide is uncoated; the injection molding guide does not contain a sizing polymer; the injection molding guide has a single composition; the injection molding guide is biodegradable; the injection molding guide is located along an edge of the barrier material; the injection molding guide is located close to an edge of the barrier material; the injection molding guide extends into the porous barrier material; the injection molding guide is 3D-printed on the barrier material; the injection molding guide is injected molded onto the barrier material.

In one aspect, the present disclosure provides methods of forming a construct and a contraceptive device of the present disclosure. For example, the present disclosure provides a method of forming a contraceptive device, the method comprising: (a) providing a construct comprising a porous barrier material affixed to an injection molding guide, the injection molding guide comprising a plurality of planar surfaces; (b) placing the construct into a die; (c) adjusting a location of at least one pin within the die so that the at least one pin contacts a surface of the injection molding guide; and (d) injecting a molten polymer into the die to form a ring structure that encases the injection molding guide. As another example, the present disclosure provides a method of forming a construct, the method comprising: 3D-printing an injection molding guide onto a porous barrier material. As yet another example, the present disclosure provides a method of forming a construct, the method comprising forming an injection molding guide, optionally by an injection molding process; and then affixing the injection molding guide to the porous barrier material. As a further example, the present disclosure provides a method of forming a contraceptive device, the method comprising: (a) providing a construct comprising a porous barrier material affixed to an injection molding guide, the injection molding guide having symmetry and comprising a plurality of planar surfaces; (b) placing the construct into a die, optionally a heated die; (c) adjusting a location of at least one pin within the die so that the at least one pin contacts a surface of the injection molding guide; (d) injecting a mixture of a two part heat curable polymer into the die to form a polymeric ring, where each of the injection molding guide and the porous barrier material is at least partially embedded within the polymeric ring; allowing the mixture of a two part heat curable polymer to cure in the mold such that the mixture of a two part heat curable polymer is transformed from a liquid state to a solid state; and (f) ejecting the contraceptive device from the die.

The present disclosure provides various aspects and embodiments of contraceptive devices, constructs useful in forming contraceptive devices and related methods for forming and using same, where these various aspects and embodiments may be combined to describe a contraceptive device, construct, and related method of the present disclosure. For example, in an aspect, the contraceptive device comprises a polymeric ring structure, an injection molding guide and a porous barrier material, where the polymer of the polymeric ring structure comprises silicone, and the polymeric ring structure further comprises ferrous gluconate, ascorbic acid, glycine and particles of poly(glycolic acid). The device may be further described by saying that encased within the silicone ring structure is an injection molding guide that comprises a lactide trimethylene carbonate polymer in which the lactide comprises greater than about 70% (w/w), e.g., 80% (w/w) of the polymer, and where the guide has a melting point above the temperature used for injection molding. The device may be further described by saying that the injection molding guide has at least one planar surface. The device may be further described by saying that it comprises a porous barrier material that is partially embedded within the polymeric ring structure, where the barrier material completely traverses the inner diameter of the ring. The device may be further described by saying that the barrier material can comprise a fibrous multifilament mesh, formed at least in part from a lactide trimethylene carbonate polymer in which the lactide comprises greater than 70% (w/w), or greater than 80% (w/w) of the polymer. The contraceptive device may be further described by saying that is has an outer diameter of about 40 mm to about 60 mm, e.g., about 45 m to about 53 mm. The device may be further described by saying that the device is not contaminated with *Pseudomonas aeruginosa, Staphylococcus aureus* or *Candida albicans*, and optionally has a bacterial endotoxin level of less than or equal to 20 EU. The device may further be described in terms of its performance properties, e.g., in an aspect the contraceptive device, when placed in simulated vaginal fluid will release ferrous ions for at least 35 days. In an aspect, the present disclosure provides a kit, containing a contraceptive device having aspects and embodiments as described herein, where the device is packaged, optionally with written instructions for use.

The present disclosure provides the following exemplary and non-exhaustive embodiments, which are numbered for convenience:

1) A contraceptive device comprising a polymeric ring, a porous barrier material and an injection molding guide, each of the injection molding guide and the porous barrier material at least partially embedded within the polymeric ring.

2) The contraceptive device of embodiment 1 wherein the barrier material is a mesh.

3) The contraceptive device of embodiment 1 wherein the barrier material is fibrous.

4) The contraceptive device of embodiments 1-3 wherein the barrier material is circular or substantially circular.

5) The contraceptive device of embodiments 1~4 wherein the barrier material has a diameter of about 40 mm to about 60 mm, e.g., from about 45 mm to about 53 mm 6) The contraceptive device of embodiments 1-5 wherein the injection molding guide is symmetrical.

7) The contraceptive device of embodiments 1-6 wherein the injection molding guide comprises a plurality of planar surfaces.

8) The contraceptive device of embodiments 1-7 wherein the injection molding guide comprises a plurality of planar surfaces, and has a corner formed by intersection of two planar surfaces, optionally wherein the injection molding guide has a corner formed by two planar surfaces intersecting at an angle, where the angle is between a 45 degree angle and a 135 degree angle, e.g., a 90 degree angle.

9) The contraceptive device of embodiments 1-8 wherein the injection molding guide is at least one of non-fibrous and non-porous.

10) The contraceptive device of embodiments 1-9 wherein the injection molding guide is completely embedded within the polymeric ring and the porous barrier material is partially embedded within the polymeric ring.

11) The contraceptive device of embodiments 1-10 wherein the injection molding guide is uncoated and/or does not contain a sizing polymer.

12) The contraceptive device of embodiments 1-11 wherein the injection molding guide is affixed to the porous barrier material.

13) The contraceptive device of embodiments 1-12 wherein the injection molding guide has a composition, and the composition is constant at each location of the injection molding guide.

14) The contraceptive device of embodiments 1-13 wherein the injection molding guide is biodegradable.

15) The contraceptive device of embodiment 1-14 wherein the injection molding guide is located along an edge of the porous barrier material.

16) The contraceptive device of embodiments 1-14 wherein the injection molding guide is located close to an edge of the porous barrier material.

17) The contraceptive device of embodiments 1-16 wherein the injection molding guide extends into the porous barrier material.

18) The contraceptive device of embodiments 1-17 wherein the injection molding guide is 3D-printed on the porous barrier material.

19) The contraceptive device of embodiments 1-17 wherein the injection molding guide is injected molded onto the porous barrier material.

20) The contraceptive device of embodiments 1-19 wherein the polymeric ring comprises an elastomeric polymer.

21) The contraceptive device of embodiments 1-20 wherein the polymeric ring encircles the porous barrier material.

22) The contraceptive device of embodiments 1-21 further comprising a biologically active agent located within the polymeric ring.

23) The contraceptive device of embodiments 1-21 further comprising a ferrous compound located within the polymeric ring.

24) The contraceptive device of embodiments 1-21 further comprising ferrous gluconate or a hydrate thereof located within the polymeric ring, optionally also further comprising ascorbic acid located within the polymeric ring.

25) A kit comprising the contraceptive device of embodiments 1-24, the kit further comprising at least one of a lubricant, a spermicidal gel, a spermicidal film, a contraceptive gel and an applicator.

26) A construct for forming a contraceptive device, such as a contraceptive device of any of embodiments 1-24, the construct comprising a porous barrier material affixed to an injection molding guide.

27) The construct of embodiment 26 wherein the barrier material is a mesh.

28) The construct of embodiments 26-27 wherein the barrier material is fibrous.

29) The construct of embodiments 26-28 wherein the barrier material is circular or is substantially circular.

30) The construct of embodiments 26-29 wherein the barrier material has a diameter of about 40 mm to about 60 mm, e.g., about 45 mm to about 53 mm 31) The construct of embodiments 26-30 wherein the injection molding guide is symmetrical.

32) The construct of embodiments 26-31 wherein the injection molding guide has a uniform cross-section at all locations around the injection molding guide.

33) The construct of embodiments 26-32 wherein the injection molding guide comprises a plurality of planar surfaces.

34) The construct of embodiments 26-33 wherein the injection molding guide has a corner formed by intersection of two planar surfaces, optionally wherein the injection molding guide has a corner formed by two planar surfaces intersecting at an angle, where the angle is between about 45 degrees and about 135 degrees, for example an angle of about 90 degrees.

35) The construct of embodiments 26-34 wherein the injection molding guide is non-fibrous and optionally is non-porous.

36) The construct of embodiments 26-35 wherein the injection molding guide has a melting point above 120° C.

37) The construct of embodiments 26-36 wherein the injection molding guide is uncoated.

38) The construct of embodiments 26-37 wherein the injection molding guide does not contain a sizing polymer.

39) The construct of embodiments 26-38 wherein the injection molding guide has a single composition at each location of the injection molding guide.

40) The construct of embodiments 26-39 wherein the injection molding guide is biodegradable.

41) The construct of embodiments 26-40 wherein the injection molding guide is located along an edge of the porous barrier material.

42) The construct of embodiments 26-40 wherein the injection molding guide is located close to an edge of the barrier material.

43) The construct of embodiments 26-42 wherein the injection molding guide extends into the porous barrier material.

44) The construct of embodiments 26-43 wherein the injection molding guide is 3D-printed on the porous barrier material.

45) The construct of embodiments 26-43 wherein the injection molding guide is injected molded onto the porous barrier material.

46) A method of forming a contraceptive device, such as a contraceptive device of any of embodiments 1-24, the method comprising:
   a. providing a construct comprising a porous barrier material affixed to an injection molding guide;
   b. placing the construct into a die;
   c. adjusting a location of at least one pin within the die so that the at least one pin contacts a surface of the injection molding guide; and
   d. injecting a molten polymer into the die to form a polymeric ring, where each of the injection molding guide and the porous barrier material is at least partially embedded within the polymeric ring.

47) The method of embodiment 46 wherein the construct is provided by a method comprising 3D-printing the injection molding guide onto the porous barrier material.

48) The method of embodiment 46 wherein the construct is provided by a method comprising:
   a. forming an injection molding guide by an injection molding process;
   b. affixing the injection molding guide to the porous barrier material.

49) A method of forming a contraceptive device, such as a contraceptive device of any of embodiments 1-24, the method comprising:
   a. providing a construct comprising a porous barrier material affixed to an injection molding guide;
   b. placing the construct into a heated die;
   c. adjusting a location of at least one pin within the die so that the at least one pin contacts a surface of the injection molding guide;
   d. injecting a mixture of a two part heat curable polymer into the die to form a polymeric ring, where each of the injection molding guide and the porous barrier material is at least partially embedded within the polymeric ring;
   e. allowing the mixture of a two part heat curable polymer to cure in the mold such that the mixture of a two part heat curable polymer is transformed from a liquid state to a solid state; and
   f. ejecting the molded product from the die.

50) The method of embodiment 49 wherein the construct is provided by a method comprising 3D-printing the injection molding guide onto the porous barrier material.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments and aspects are set forth in the description below. The features illustrated or described in connection with one exemplary embodiment or aspect may be combined with the features of other embodiments or aspects. Thus, any of the various embodiments or aspects described herein can be combined to provide further embodiments of the present disclosure. Features of the embodiments and aspects can be modified, if necessary, to employ concepts of the various patents, applications and publications as identified herein to provide yet further embodiments. Other features, objects and advantages will be apparent from the description, the drawings, and the claims.

BRIEF DESCRIPTION OF THE FIGURES

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 4 shows a schematic of an exemplary injection molding guide (1) provided on a porous barrier material (2) of an exemplary contraceptive medical device disclosed herein.

FIGS. 5A and 5B each show a schematic of an exemplary injection molding guide (1) provided on a porous barrier material (2) of an exemplary contraceptive medical device disclosed herein.

FIG. 6B shows a full cross-sectional view of the construct of FIG. 6A as viewed through the line B shown in FIG. 6A, and FIG. 6C shows a partial cross-sectional view of the construct of FIG. 6A, and in particular the part of the cross-sectional view enclosed within the area denoted C in FIG. 6B.

DETAILED DESCRIPTION

Figure 1:
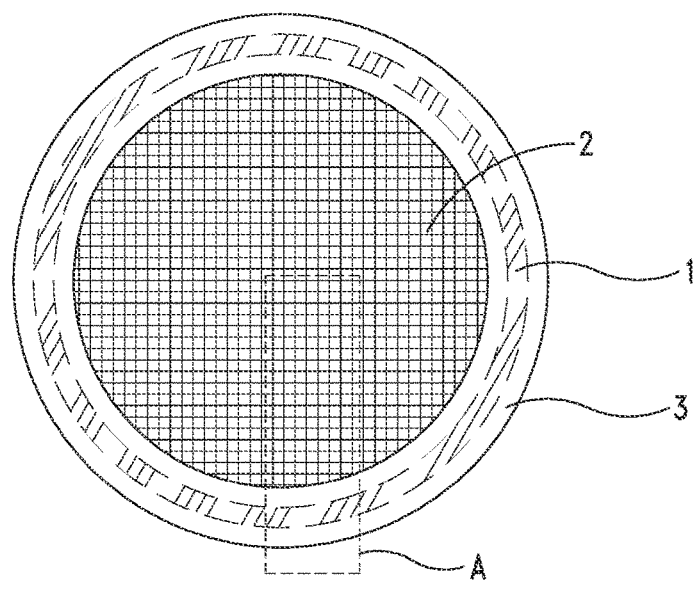
FIG. 1 shows a top view of an exemplary contraceptive medical device disclosed herein, illustrating an injection molding guide (1), a porous barrier material (2), and a ring structure (3).

Disclosed herein are contraceptive medical devices, also referred to as contraceptive devices, methods of making and using the contraceptive devices, and constructs useful to make the contraceptive devices. In one aspect the present disclosure provides a contraceptive device comprising a barrier material, an injection molding guide and a ring structure. For example, the present disclosure provides a contraceptive device comprising a polymeric ring, a porous barrier material and an injection molding guide, each of the injection molding guide and the porous barrier material at least partially embedded within the polymeric ring. The barrier material has the ability to retard the passage of sperm through the barrier material but does not prevent vaginal fluid from passing through the barrier material. In an aspect, the barrier material is porous, or at least partially porous, having a pore size such that sperm is retarded from crossing the barrier material but vaginal fluid can cross the porous barrier material. The polymeric ring facilitates maintaining the contraceptive device in a fixed position in vivo, and in particular in the vaginal canal. The injection molding guide facilitates efficient manufacture of the contraceptive device. Optionally, the contraceptive device further comprises a biologically active agent, and further optionally comprises one or more of an excipient, a pH modulator, an antioxidant, a preservative, and a release modifying agent that modulates the release of the biologically active agent. Optionally, the biologically active agent is a component of a composition, where the composition functions to reduce the potential of sperm to enter the cervix. In one aspect the present disclosure provides a method of making a contraceptive device comprising a barrier material, an injection molding guide and a polymeric ring, where the method includes forming the polymeric ring by injection molding the polymeric ring portion of the contraceptive device, the injection molding making use of the injection molding guide. In another aspect, the present disclosure provides a method of achieving contraception comprising inserting the contraceptive device into a vaginal canal.

In another aspect the present disclosure provides a construct comprising the barrier material and the injection molding guide, where the construct can serve as a precursor to the contraceptive device and be a part of the contraceptive device. In another aspect, the present disclosure provides a method of preparing the construct, and also provides a method of preparing the contraceptive device using the construct. In one aspect, the construct is placed into a cavity, optionally called the mold or die, of an injection molding machine, whereupon two or more pins of the injection molding machine engage with the injection molding guide of the construct, where the pins serve to position and/or secure the construct in a desired location within in the mold during the injection molding of the polymeric ring. In one aspect, the injection molding guide has a symmetrical shape so that the pins engage with the injection molding guide in a uniform manner regardless of where the construct is initially placed within the chamber. In other words, when a plurality of pins uniformly extend into the mold and engage with the injection molding guide, each of the plurality of pins engages equally with the injection molding guide, e.g., one pin of the plurality does not need to extend further into the mold to engage with the injection molding guide compared to any other of the plurality of engaging pins. This degree of symmetry of the injection molding guide facilitates efficient manufacture of the contraceptive device of the present disclosure.

FIG. 1 shows a schematic top view of an exemplary contraceptive device of the present disclosure, comprising an injection molding guide (1), a porous barrier material (2), and a ring structure (3) which may be referred to herein as the polymeric ring. The injection molding guide (1) is actually embedded within the ring structure (3), however in the depiction of FIG. 1, the location of the injection molding guide (1) within the ring structure (3) is illustrated by the dashed lines within the ring structure (3). As shown in FIG. 1, the injection molding guide (1) has an appearance of an annular ring when viewed from the top of the contraceptive device.

Figure 2:
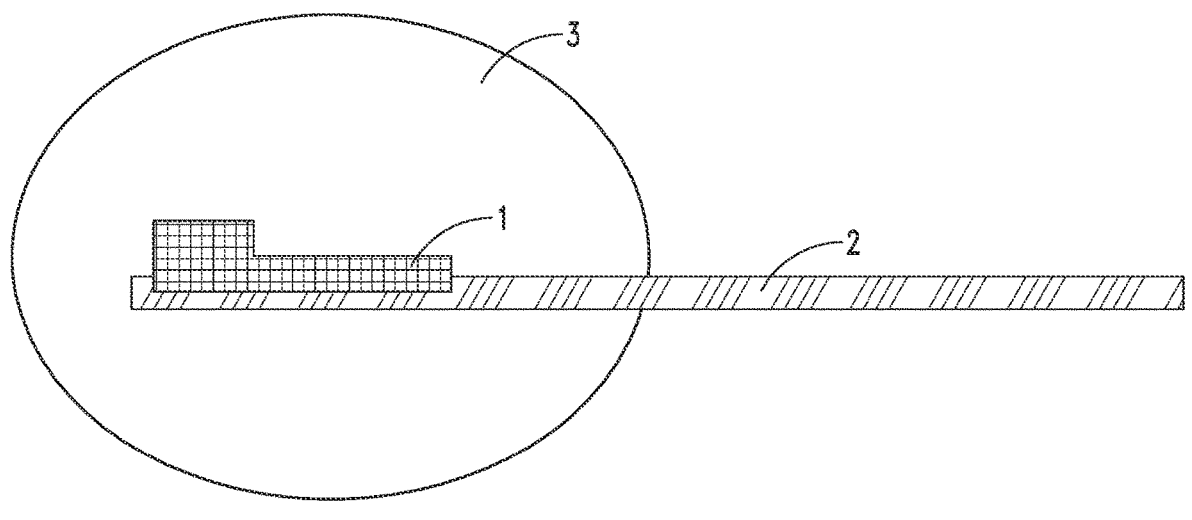
FIG. 2 shows a schematic of a side view of a portion of an exemplary contraceptive medical device disclosed herein, and more specifically the portion identified by "A" in FIG. 1, illustrating an injection molding guide (1), a porous barrier material (2), and a ring structure (3).

FIG. 2 shows a schematic of a partial side view of the exemplary contraceptive device shown in FIG. 1, and in particular the partial side view of the region identified as region "A" in FIG. 1, where this partial side view shows a cross-section of the contraceptive device including a cross-section of a portion of an exemplary injection molding guide (1), a cross-section of a portion of the porous barrier material (2), and a cross-section of a portion of the ring structure (3). As shown in FIG. 2, an exemplary injection molding guide (1) may include an L shape including a plurality of planar surfaces when viewed in partial cross section, in this case five planar surfaces. Thus, an injection molding guide of the present disclosure may have the appearance of an annular ring (when viewed from the top) and include a plurality of planar surfaces (when viewed in cross section). In one embodiment, the injection molding device has a base surface which is placed adjacent to the porous barrier material, where the base surface is a planar surface, and where the base surface may optionally extend into the openings of the porous barrier material as shown in FIG. 2.

The contraceptive device of the present disclosure may be prepared from, and may optionally comprise a construct comprising the barrier material in contact with, and optionally affixed to, the injection molding guide. The construct is particularly useful in a method of the present disclosure to form the contraceptive device of the present disclosure. In the method, the ring structure is added to the construct which comprises the barrier material and the injection molding guide.

In one aspect, the construct is placed within a cavity, also referred to as a mold or die or chamber, which can receive molten polymer during an injection molding process. The molten polymer is injected into the mold so as to form the ring structure. During this injection molding process, it is desirable to hold the construct securely in place, so that neither the barrier material nor the injection molding guide moves while the molten polymer is injected under force into the mold. To this end, after the construct is placed in the mold, a plurality of movable pins are brought into contact with a surface of the injection molding guide, e.g., a flat surface of each of the pins is pressed against a flat surface of the injection molding guide, so that the pins secure the injection molding guide in a fixed position within the mold. Thus, an injection molding guide has a configuration that allows it to be centered in an injection molding die. An injection molding guide can also allow the pins of an injection molding die to contact an injection molding guide directly rather than the mesh. This reduces the negative mechanical impact on the mesh that occurs when the pins are placed into the mesh. Since the barrier material is held between the bottom of the mold and the injection molding guide, and is optionally securely affixed to the injection molding guide, the barrier material becomes secured in place within the mold when the pins secure the injection molding guide within the mold. After the pins are brought into contact with the injection molding guide, molten polymer is injected into the mold so as to surround the injection molding guide to at least partially encase the injection molding guide. Upon cooling, the molten polymer forms the ring structure of the contraceptive device of the present disclosure.

In one aspect, the ring structure is added to the construct which comprises the barrier material and the injection molding guide. In the method, the construct is placed within a heated or heatable cavity, also referred to as a mold or chamber, which can receive a mixture of a two part heat curable polymer during an injection molding process. The liquid polymer mixture is injected into the mold so as to form the ring structure. During this injection molding process, it is desirable to hold the construct securely in place, so that neither the barrier material nor the injection molding guide moves while the liquid polymer mixture is injected under force into the mold. To this end, after the construct is positioned in the mold, a set of movable pins are brought into contact with one or more surfaces, e.g., planar surfaces, of the injection molding guide, and a surface of each of the pins is pressed against a surface of the injection molding guide, so that the pins secure the injection molding guide in a fixed position within the mold. Thus, an injection molding guide has a configuration that allows it to be positioned in a predetermined location within an injection molding die, and then held securely in place at the predetermined location during the injection molding process which forms the polymeric ring. The injection molding guide preferably has a symmetry to its shape which facilitates this injection molding process. An injection molding guide may also allow the pins of an injection molding die to contact an injection molding guide directly rather than the mesh. This reduces the negative mechanical impact on the mesh that occurs in the event the pins engage, i.e., are placed against, the mesh. Since the barrier material is held between the bottom of the mold and the injection molding guide, and is optionally securely affixed to the injection molding guide, the barrier material becomes secured in place within the mold when the pins secure the injection molding guide within the mold. After the pins are brought into contact with the injection molding guide, the liquid polymer mixture is injected into the mold so as to surround the injection molding guide to at least partially encase the injection molding guide, and optionally to completely encase the injection molding guide. The liquid polymer mixture is kept in the heated mold at a specified temperature for a period of time such that the liquid polymer mixture cures (also known as crosslinks) to a solid polymer form wherein the solid polymer has formed the ring structure of the contraceptive device of the present disclosure. The formed contraceptive device is then ejected out of the mold.

The ring structure desirably forms the outer edge of the contraceptive device of the present disclosure. Thus, the polymeric ring may surround the perimeter of the porous barrier material. Accordingly, in both the construct and the contraceptive device, the injection molding guide is desirably located at or near the outer edge of the barrier material. The outer edges of each of the barrier material and the injection molding guide may be described as circular, as illustrated in FIG. 1. Optionally, the barrier material is substantially circular.

In one embodiment, the outer edge of the injection molding guide coincides with, i.e., is flush with, the outer edge of the barrier material. In another embodiment, which is illustrated in FIG. 2, the outer edge of the injection molding guide is slightly within the outer edge of the barrier material, e.g., in embodiments, 1, or 2, or 3, or 4, or 5, or 6, or 7, or 8, or 9, or 10 mm of barrier material extend beyond the outer edge of the injection molding guide. In another embodiment, the outer edge of the injection molding guide is slightly beyond or outside the outer edge of the barrier material, e.g., in embodiments, 1, or 2, or 3, or 4, or 5, or 6, or 7, or 8, or 9, or 10 mm of the injection molding guide extend beyond the outer edge of the barrier material.

Barrier Material

The barrier material of the present disclosure has the ability to retard the passage of sperm across the barrier material but does not substantially retard the ability of vaginal fluid to pass through the barrier material.

The barrier material can comprise one or more polymers. Polymers that can be used in the presently disclosed device may be non-absorbable, absorbable, or a combination thereof. Suitable absorbable and non-absorbable polymers are described later herein. In one aspect the barrier material can comprise a metal. For example, the mesh may be a wire mesh. In one aspect, the mesh is a stainless-steel mesh.

The barrier material may be circular, and thus have a diameter. In one embodiment, the diameter of the barrier material is within the range of about 40 to 60 mm. The barrier material may have a diameter of at least 40 mm, e.g., at least 41 mm, or at least 42 mm, or at least 43 mm, or at least 44 mm, or at least 45 mm, or at least 46 mm, or at least 47 mm, or at least 48 mm. The barrier material may have a diameter of less than 60 mm, e.g., less than 59 mm, or less than 58 mm, or less than 57 mm, or less than 56 mm, or less than 55 mm, or less than 54 mm, or less than 53 mm, or less than 53 mm, or less than 52 mm, or less than 51 mm. In embodiments, the barrier material has a diameter within a range selected from any of the above-listed minimum diameters extending to any of the above-listed maximum diameters, e.g., a diameter within the range of about 45 mm to about 53 mm. The barrier material may be described as substantially flat, in that the diameter is much larger than the thickness of the barrier material. In an aspect, the barrier material may be non-circular. The barrier mesh may be rectangular, square, pentagonal, hexagonal, heptagonal or octagonal.

The physical barrier material of the contraceptive device can be in the form of a knitted or woven mesh. The knitted or woven mesh can comprise one or more fibers or yarns. In embodiments, the barrier material has a form selected from a porous mesh, an open cell foam, a porous non-woven material, and a porous film. In one embodiment, the barrier material is porous. In one embodiment, the barrier material is a mesh. In one embodiment, the barrier material is fibrous. In one embodiment, the barrier material is a mesh formed from fibers, i.e., is a fibrous mesh.

Absorbable and non-absorbable polymers as described herein can be formed into suitable fibers for forming a barrier material. The fibers can be manufactured from the polymers through an extrusion process. The extrusion process can comprise heating the polymer to a point at which it can flow and then forcing the polymer through an opening of a defined shape and size. The fibers can be round, oval, square, rectangular, irregular, bilobal or trilobal.

In optional embodiments, the fiber can have a cross-sectional dimension of 5 μm to 600 μm. In an aspect, the fiber cross sectional dimension is 20 μm to 300 μm. A monofilament fiber is a single fiber. A yarn that comprises a monofilament fiber can be referred to as a monofilament yarn. A preferred cross-section dimension of a monofilament is 40 μm to 400 μm. A more preferred cross-section dimension of a monofilament is 80 μm to 200 μm.

In one aspect, two or more fibers can be formed into a multifilament yarn, and this yarn used to form the barrier material. In one aspect, the yarn can comprise 2 to 100 fibers. In a preferred aspect, the yarn can comprise 30 to 90 fibers. In an aspect, the yarn can comprise 86 fibers. In another aspect, the yarn can comprise 43 fibers. The final yarn can be prepared by plying two or more yarns together. In an aspect, the number of fibers of each yarn to be plied together are the same. For example, a 43 fiber multifilament yarn can be plied together with a second 43 fiber multifilament yarn to form a plied yarn that comprises 86 fibers. In another aspect, the number of fibers of each yarn to be plied together are different. For example, a 43 fiber multifilament yarn can be plied together with a second 35 fiber multifilament yarn to form a plied yarn that comprises 78 fibers. The plied yarn can have a total filament count of 2 to 200. In an aspect, the total filament count is 40 to 120. In an aspect, the plied yarn has 86 fibers. The multifilament yarn can be manufactured from fibers of the same composition or they can be manufactured using fibers of two or more different compositions. This will result in a blended yarn. In one aspect, the yarn can be absorbable. In another aspect, the yarn can non-absorbable. In another aspect, the yarn can comprise fibers that are absorbable and fibers that are non-absorbable.

The multifilament yarn can be prepared without twisting the fibers. In one aspect the yarn can be a flat yarn. In one aspect, the yarn can be twisted. In one aspect, the yarn can comprise 1 to 7 twists per inch (TPI). In a preferred aspect, the yarn can comprise 2-6 TPI. In one aspect, that yarn can comprise an average of 2 TPI, 3 TPI, 4TPI, 5 TPI, or 6 TPI.

Optionally, the fiber or fibers may undergo orientation by drawing the fibers, prior to their use in forming the barrier material.

In an aspect, the yarn can be texturized. Textured yarn is produced using various twisting, mechanical and heat setting techniques which generate a crimped effect making the yarn thicker and softer, as well as potentially giving it the ability to stretch. In an aspect, the yarn can be twisted, heat set in the twisted configuration and then untwisted. The yarn will then assume a spiral type shape which will give the yarn stretchiness and fluffiness. In an aspect, the yarn can be crimped. The yarn is packed tightly into a chamber of a predefined shape and is then heat set while in this constrained conformation. Once released from the confined configuration, the yarn takes on a stretchable form. In an aspect, the yarn can be looped. A looped yarn is manufactured by exposing the multifilament yarn to a jet of pressurized air in a technique known as air-jet texturizing or air texturizing. Each of these yarns may be used in a barrier material of the construct or contraceptive device of the present disclosure.

In an aspect, the yarn of the barrier material can be in the form of a staple yarn. The staple yarn is formed by taking relatively short lengths of a fiber, carding the fibers and then drawing and spinning to produce a yarn. If highly aligned fibers are desired, the carded fibers can be combed to further align the fibers. Staple yarn can be manufactured from fibers of the same composition or they can be manufactured using fibers of two or more different compositions. This will result in a blended staple yarn. In one aspect, the staple yarn can be absorbable. In another aspect, the staple yarn can be non-absorbable. In another aspect, the staple yarn can comprise fibers that are absorbable and fibers that are non-absorbable. In an aspect, the yarn can be an abraded yarn.

The denier of a fiber or yarn is measured in terms of mass in grams of 9000 meters of the fiber or yarn. For monofilament fibers or multifilament yarns, the denier of the fiber or yarn used to form the barrier material may be between 1 to 800. In one aspect, the denier of a fiber or yarn is between 30 and 300. In another aspect, the denier is between 50 and 250. Another way to characterize a fiber or yarn is using denier per filament. The denier per filament (DPF) is calculated by dividing the yarn denier by the number of filaments that make up the yarn. In one aspect, the DPF of a yarn or fiber used to form the barrier material is between 1 and 25. In another aspect, the DPF is between 2 and 10.

The fibers of the barrier material may further comprise a dye. In one aspect, the dye can be incorporated into the fiber or yarn during the extrusion process. In another aspect, the dye may be applied as a coating onto the finished fiber or yarn. In another aspect, the dye can be incorporated into the fiber or yarn by dyeing the material. The dyeing process may be achieved by immersing the fiber or yarn into a solution of the dye and allowing the dye to diffuse into the fiber or yarn. Examples of dyes that can be used include but are not limited to D&C violet No. 2, (phthalocyaninato[2]) copper, logwood extract, D&C green No. 5, D&C green No. 6, Chromium-cobalt-aluminum oxide, FD&C blue No. 2, and D&C blue No. 6.

Following extrusion of the fiber or fibers, a spin finish can be applied to the fiber prior to forming the fibers into a barrier material. The spin finish can act as a lubricant, an anti-oxidant or an antistatic agent. Spin finish materials can include but are not limited to glycerine, poly(ethylene glycol) dioleate Esterol 244, magnesium stearate, isocetyl stearate, an alkyl stearate, an alcohol ethoxylate or alkylphenol ethoxylate, butyl stearate, alkyl polyoxyethylene carboxylate ester, polyalkylene glycol (200) monolaurate, polyalkylene glycol (600) monoisostearate, ethoxylated-propoxylated butyl alcohol, POE(5) lauryl potassium phosphate, POE(30) castor oil, Lurol 1187 (Goulston Inc., 700 N. Johnson Street, Monroe, N.C. 28110), Lurol PT-6A, LUROL FR-L987, LUROL PS-14135, LUROL PS-11158, LUROL PS-662, LUROL SF-14974, LUROL PS-9725, LUROL-SF-13191, LUROL SF-15361, LUROL SF-15704, LUROL SF-15628, PS-662, PS-13460, LUROL PP-912, Lurol® SF-563, Lurol® SF-565, Lurol® SF-567, Lurol P1.801 (Goulston), Lurol PT-L216 (Goulston), Stantex 6457 (Pulcrachem), Esterol PF-790 (Bozzeto GmbH), Estesol TXB (Bozzetto Group), and Filapan CTC (Boehme). Spin finishes from Dow such as SYNALOX™ 50-30B and SYNALOX™ 50-50B could also be used. In an aspect, the spin finish is Lurol PT-6A. In once aspect, the spin finish is glycerine.

In one aspect, the barrier material is a knitted mesh. The knitted mesh may comprise one or more non-absorbable fibers or yarn, one or more absorbable fiber or yarn or a combination thereof. Warp knitting or weft knitting can be used to manufacture the knitted mesh. For warp knitted barriers, conventional and known warp knitting apparatus and techniques can be used. Such apparatus and techniques are described in Knitting Technology, A comprehensive handbook and practical guide by David J Spencer (Third Edition, 2001 Woodhead Publishing Limited and Technomic Publishing Company Inc, ISBN 1 85573 33 1) the contents of which are incorporated by reference. A tricot knitting machine can be used to knit the barrier material. The tricot machine can have two, three or four guide bars. In a preferred aspect, the machine has two guide bars. A raschel knitting machine can be used to knit the barrier material.

The structure of the knitted mesh of the barrier material may be defined for any given yarn in terms of the number of courses per inch and the number of wales per inch as well as the specific knit design. In one aspect, the course per inch of the knitted barrier is in the range of 4 to 80. In another aspect, the course per inch is 10 to 40. In another aspect, the course per inch is 20 to 40. In one aspect, the barrier knitted mesh has 9 to 44 wales per inch. In another aspect, the barrier knitted mesh has 15 to 35 wales per inch. In another aspect, the knitted barrier mesh has 15 to 25 wales per inch.

The knitted barrier mesh knit pattern may include but is not limited to a locknit, reverse locknit, Tricot jersey, tricot satin, half tricot, tricot two bar, sharkskin, or queenscord pattern. In another aspect, the knit pattern can be a marquisette. The barrier material comprise a knit pattern similar to that of part numbers PETKM2002, PETKM2004, PETKM2006, PETKM2007, PETKM2008, PETKM2009, PETKM3002, PETKM3003, PETKM7002, PETKM14002, PPKM301, PPKM302, PPKM403, PPKM404, PPKM405, PPKM406, PPKM407, PPKM409, PPKM501, PPKM502B, PPKM503, PPKM505, PPKM506BS, PPKM601, PPKM603, PPKM604, PPKM605, PPKM606, PPKM607BS, PPKM608B, PPKM801, PPKM802 AND PPKM 807 from Surgical Mesh (72 Grays Bridge Road Unit D1, Brookfield, Connecticut, 06804, USA). In an aspect, the barrier material has a knit pattern similar to that of part numbers RJ27, XT34, XA90, TG77, TF40, RG90, RG26, RG06, RF99, RB88, RB61AF, PR95, PQ15, NZ74, NX91, NT55, NP61, NK50A, NK47A, NJ85, ND29, ND27, NB63, N98, LF2, AROWLN, NZ11, RC08, PV57 from Apex Mills (168 Doughty Boulevard, Inwood, NY 11096, USA).

In an aspect, the barrier material is a knitted material with a course per inch of about 38, having a two-bar tricot knit pattern.

The barrier material of the contraceptive device may also be manufactured using a weaving process. In an aspect, ends per inch of the woven barrier is in the range of 4 to 40. In another aspect, the end per inch is 5 to 20. The woven barrier material may have 2 to 44 picks per inch. In another aspect, the woven barrier material may have 3 to 20 picks per inch. Optionally, the woven barrier material has the same weft material and warp material. However, in one aspect, the weft material and the warp material are different. In an aspect, material used to manufacture the woven barrier can be absorbable, non-absorbable or a combination thereof. The woven pattern of the barrier material may be similar to that of part numbers PETWM707001, PETWM757501 from Surgical Mesh (72 Grays Bridge Road Unit D1, Brookfield, Connecticut, 06804, USA).

The barrier material may be manufactured using a melt blown process. According to this process, thermoplastic polymer granules are melted and passed into an extruder. The molten polymer is then passed into a nozzle block that contains one or more outlets for a heated gas. After passing through the extruder nozzle tip, the polymer is drawn into fibers by the compressed heated gas. The fibers are blown onto a gas permeable mesh belt to complete the formation of the melt blown fabric. The gas that can be used can include but is not limited to air, nitrogen, argon or a combination of two or more of the gases.

The barrier material manufactured using the melt blown process can comprise a single polymer or it can comprise two or more polymers. In an aspect, two different polymer granules are loaded into the extruder simultaneously to produce a single barrier material with fibers that comprise a blend of two or more polymers. In another aspect, the barrier material has a laminate structure. In one embodiment, the laminate structure can be manufactured by preparing a first layer of melt blown material and then forming a second layer of melt blown fibers by blowing the second layer on top of the first layer. This will form a bi-laminate structure. This process can be repeated such that a third layer is applied to the second layer, in order to form a tri-laminate structure. The two layers of the bi-laminate structure can comprise the same polymer composition or the two layers can comprise different polymer compositions. For the tri-laminate, the layers may comprise the same polymer composition, different polymer compositions, or two layers may have the same polymer composition that is different from the third layer.

The melt blown layer may be formed on a polymeric mesh that is knitted, woven or non-woven. In an aspect, a bi-laminate structure can be prepared with the melt blown layer overlaying or interpenetrating the mesh layer. In another aspect, a tri-laminate structure can be prepared with the mesh sandwiched between two melt blown layers. In another aspect, a second melt blown layer can be applied to the top of the first melt blown layer to give a tri-laminate structure with a mesh base layer followed by two melt blown layers. In an aspect, the polymer composition of the mesh and the melt blown layers are the same. In another aspect, the polymer composition of the mesh and the melt blown layers are different.

The porosity and pore size of the melt blown layer can be controlled by a combination of nozzle diameter, extrusion temperature, compressed gas temperature, polymer extrusion speed, compressed heated gas flow rate, distance of the nozzle from the collection mesh and the speed of the collection mesh. For a laminate structure, the pores of the layers can be about the same size. In an aspect, the pores of the laminate layers can be different.

The barrier material of the contraceptive device can be manufactured using a spunbond process, a nonwoven carded process, nonwoven airlaid process or a nonwoven wetlaid process. In another aspect, a combination of processes can be used to manufacture the barrier material. For example, the barrier material may be manufactured using a melt blow process and a spunbond process. Melt blown and spunbond processes may be used to manufacture a spun-melt-spun laminate structure. The mechanical properties of the materials produced using one of these processes may be improved by using a bonding process. Thermal bonding, sonic bonding, chemical bonding or mechanical bonding are suitable options. A thermal bonding process may include but is not limited to flat bonding, point bonding or thru-air bonding. For flat bonding, heat and pressure are applied to the material in the form of a flat calendar. Flat bonding applies a heated roll with a specific pattern embossed into the roll. The fibers are then bonded together at the points where the pattern of the roller contacts the fibers. The thru-air bonding process draws the fabric through a heated drum which created bonds throughout the fabric.

In one aspect, the barrier material is manufactured using an electrospinning process. In this process, a solution of a polymer is pumped through a nozzle and is collected on a collection plate. The process is run with a large potential difference between the nozzle and the collection plate. The material on the collection plate is in the format of a nonwoven mesh with fibers in the 0.2-50 μm range. In an aspect, the collection plate can be a drum that is rotated. In an aspect, the drum can be rotated at a speed of about 10 rpm up to about 500 rpm. In an aspect, the fiber can be aligned by increasing the speed of the collection drum. The greater the rotational speed, the higher the degree of alignment of the resultant fiber. In one aspect, the drum can be rotated at greater than about 500 rpm to about 1000 rpm.

In an aspect, the electrospun material can be manufactured using a blend of two or more polymer solutions. In another aspect, the material can be manufactured using two or more separate polymer solutions that are pumped through separate and different nozzles. The electrospun barrier material may comprise one or more absorbable polymers, one or more non-absorbable polymers or a combination thereof.

In one aspect, the barrier material is manufactured in the form of a film that has a series of holes or fenestrations in the film such that the film can allow water to pass through the film. The film may be prepared by, for example, solvent casting, extrusion or mechanical compression. The holes in the film may be introduced by any of mechanical perforation of the film, laser drilling of holes or by the use or a porogen that is dissolved out of the film to leave behind a porous structure. Porogens that can be used include but are not limited to sodium chloride, sucrose, or a polymer that is soluble in a non-solvent for the polymer used to manufacture the film. The fenestrations may be introduced by stamping or roller cutting fenestrations into the film. The film based barrier material may comprise one or more absorbable polymers, one or more non-absorbable polymers or a combination thereof.

In one aspect, the barrier material is prepared by laminating two or more barrier materials together. In an aspect, the barrier materials used for lamination are manufactured using the same process. In another aspect, the barrier materials used for lamination are manufactured using different processes. For example, a knitted mesh can be laminated with a melt blown mesh. Any combination of the barrier material using different manufacturing process can be laminated together to form a final barrier material that comprises the contraceptive device or precursor construct thereto.

In one aspect, the barrier material used in a contraceptive device or precursor construct thereto comprises a porous material. The barrier material has porosity such that water can pass through the barrier material. In another aspect, the barrier material can allow simulated vaginal fluid, as defined in Marques et al (Marques, M. R. C., Loebenberg, R., & Almukainzi, M. (2011) Dissolution Technologies, 18(3), 15-28) to pass through the barrier material. In an aspect, the aqueous solution can pass through the barrier membrane at a rate of at least 50 mL per minute. In an aspect, the barrier material has a flow rate of 2 gallons/minute/square foot to 500 gallons/minute/square foot for water passing through the barrier membrane. In an aspect, the barrier material has a flow rate of 10 gallons/minute/square foot to 300 gallons/minute/square foot for water passing through the barrier membrane. In an aspect, the barrier material can have a flow rate of 50 gallons/minute/square foot to 250 gallons/minute/square foot for water passing through the barrier membrane. A barrier material can comprise a range of pore sizes. The pore size, as measured by the short width distance between the one side of the pore and the opposite side of the pore, can be 50 μm to 500 μm. In an aspect the average pore size is 80 μm to 300 μm. In an aspect, the average pore size is 90 μm to 250 μm. In an aspect the pore size can be homogeneous with a relative standard deviation of the measured pore size of less than 10%. In an aspect, the pore size can be non-homogeneous with a relative standard deviation of the measured pore size of greater than 10%.

A barrier material can undergo post manufacture treatment. This treatment can include but is not limited to washing, thermal treatment, surface treatment, coating and sterilization.

A barrier material can be washed in a non-solvent for the polymer. The solvent used for washing the mesh can be a non-aqueous solvent, an aqueous solvent or a combination of an aqueous and a non-aqueous solvent. Non-aqueous solvent can include but are not limited to methanol, ethanol, 2-isopropyl alcohol, acetone, ethyl acetate, methyl ethyl ketone, methyl tert-butyl ether, toluene, cyclohexane and hexane. An aqueous solvent can include but is not limited to water, deionized water, saline, phosphate buffered saline, a basic aqueous solution, a sodium hydroxide solution, an acidic aqueous solution and a hydrochloric acid solution.

A barrier material can be washed in a batch process or using a continuous process. The washing step can be used to remove particulates, impurities, fiber lubricants, spin finish, extrusion aids or a combination of these. In an aspect, the barrier material can be washed in a batch process with isopropyl alcohol. The washing step can be repeated one or more times until the desired specification is met. In an aspect, the barrier material is washed with isopropyl alcohol at least two time in order to reduce the residual fiber lubricant or spin finish to a level that is non-cytotoxic in an in-vitro cellular assay. In an aspect, the washing process can reduce the fiber lubricant or spin finish content by at least 50% on a weight by weight basis as compared to the unwashed barrier material. In another aspect, the washing process can reduce the fiber lubricant or spin finish content by at least 90% on a weight by weight basis as compared to the unwashed barrier material. In an aspect, the residual fiber lubricant or spin finish in the final barrier material can be less than about 4% (w/w), about 3% (w/w), about 2% (w/w), about 1% (w/w) or about 0.5% (w/w). In a preferred aspect, the residual fiber lubricant or spin finish in the final barrier material can be less than about 0.2% (w/w). In an aspect, the residual fiber lubricant or spin finish in the final barrier material can be greater than about 0.01% (w/w) and less than about 0.2% (w/w). In an aspect, the final barrier material does not comprise a fiber lubricant or spin finish.

After washing, a barrier material can be air dried, dried under a flow of gas, dried under a flow of heated gas, dried under vacuum, dried under vacuum and heat or a combination of the above.

A barrier material can be subjected to a heat treatment. A barrier material can be subject to heat setting or annealing. For the heat setting process, a barrier material is heated for a period of time above the glass transition temperature (Tg) of the material. The material is then cooled to room temperature. The heat setting process increases the stability of the barrier material, e.g., it may increase the thermal stability of the barrier material, and/or it may increase the physical stability of the barrier material. In one embodiment, the heat setting process increases the mechanical stability of the barrier material. The heat setting of the barrier material reduces the percentage that the barrier will change dimensional shape as compared to barrier material that was not heat set. Parameters that can be used to modify the heat setting of the barrier material include temperature, duration of exposure to the specified temperature, the tension applied to the barrier material during heat setting and during the cooling period, the humidity of the environment used for heat setting and the medium used for heat setting. In an aspect, the heat setting medium can be heated air. In an aspect, the heat setting medium can be a non-solvent liquid. In an aspect, the heat setting medium can be a heated surface. The heat setting process can be performed on a continuous process or a batch process. A tenter frame can be used to perform heat setting on a continuous basis. A pin frame can be used to heat set the barrier material in a batch process. In an aspect, the barrier material can be heat set by passing the material through a set of heated calendar rollers. The pressure applied to the barrier material during the passage through the calendar rollers can be adjusted. The porosity of the barrier material can also be modified by passing the barrier material through heated calendar rollers.

Injection Molding Guide

In an aspect, the injection molding guide is not attached to the barrier material prior to the injection molding of the ring component. However, in an aspect, the injection molding guide is affixed to the barrier material so as to form a construct, where the construct is placed in the die of an injection molding device prior to the injection molding of the ring component. When the injection molding guide is affixed to the barrier material, an entire surface of the injection molding guide may be affixed to the barrier material, or in an aspect, less than an entire surface, e.g., only one or more portions of a surface, may be affixed to the barrier material, in order to retain the injection molding guide in contact with the barrier material during injection molding of the ring component.

An injection molding guide may be a solid, non-fibrous or fibrous layer. In one aspect, the injection molding guide is non-fibrous. The injection molding guide may comprise a polymer, and optionally may be entirely formed from a polymer. In one aspect the injection molding guide comprises a thermoplastic polymer. In one aspect the injection molding guide comprises a thermoset polymer, for example, a heat cured, also known as a heat set, polymer, which refers to a polymer that was formed by mixing and then heating two inter-reactive polymers (heat curable mixture) to form a so-called heat cured polymer. In one aspect the injection molding guide is non-fibrous and comprises a heat cured polymer.

When it is attached to the barrier material so as to form a construct, an injection molding guide may be, or is, attached to the barrier material towards the outer edge of the barrier material. An injection molding guide is attached to the barrier material so that the barrier material may be readily centered in an injection molding mold and retained in a desired and predetermined position during the molding of the ring portion of the contraceptive device.

An injection molding guide can have various cross-sectional shapes. An injection molding guide cross-sectional shape can include but is not limited to a square, a rectangular shape, an L-shape, a T-shape an off-set T-shape, a U-shape, a V-shape, a partial V-shape, a hemisphere, or an irregular shape. In cross-section, the injection molding guide having the shape of a square or a rectangle will have four corners, the injection molding guide having the shape of an L will have six corners, and the injection molding guide having the shape of a T will have eight corners. In an aspect, an injection molding guide can be attached to the barrier on only one side of the barrier material. In another aspect, an injection molding guide can be attached to both sides of the barrier material. The injection molding guide may cover a part of a surface of the barrier material, where a part of the barrier material that is not covered by the injection molding guide is porous as described herein.

The injection molding guide of the constructs and contraceptive devices of the present disclosure may be prepared by any convenient means. For example, the injection molding guide may be a plastic part prepared by injection molding. When the injection molding guide is prepared independently of the barrier material, then the injection molding guide will be affixed to the barrier material using, e.g., an adhesive. As another example, the injection molding guide may be prepared by 3D-printing, and then affixed to the barrier material. Any of 3D-printing, extrusion, solvent casting or injection molding are suitable means to manufacture the injection molding guide. In one aspect, the injection molding guide comprises a thermoplastic polymer. In one aspect, the injection molding guide comprises a thermoset polymer. In one aspect, the injection molding guide is non-fibrous and comprises a thermoplastic polymer. In one aspect, the injection molding guide is non-fibrous and comprises a thermoset polymer, e.g., a heat cured polymer.

As mentioned above, an injection molding guide can be manufactured separately and then attached to the barrier so as to affix the injection molding guide to the barrier material. The formed injection molding guide can be attached to the barrier using an adhesive. The adhesive that can be used includes but is not limited to a solvent based-adhesive, a contact adhesive, a hot melt adhesive, a 2-part adhesive or a reactive adhesive such as a cyanoacrylate adhesive. In an aspect, the solvent-based adhesive can be a polyester dissolved in acetone or dichloromethane. In an aspect, the polyester can be a polymer that comprises lactide residues. In an aspect, the polyester can be a polymer that comprises ε-caprolactone residues. The formed injection molding guide can be attached to the barrier using an ultrasonic welding process, a laser welding process, an embroidery process or a hot stamping process where the one surface of an injection molding guide is heated and then press fitted onto the barrier.

In one embodiment, the injection molding guide is 3D-printed directly onto the barrier material. The 3D-printing process may optionally utilize fused fiber filament (FFF) 3D printing. In this embodiment, the barrier material may be porous, so that the molten polymer used in the 3D-printing process will flow, to some extent, into the openings of the barrier material. Upon cooling, the 3D-printing polymer will harden and encase a portion of the barrier material. In this way, the injection molding guide becomes physically affixed to the barrier material. In this embodiment, the melting point of the polymer used to form the injection molding guide should not be substantially higher than the melting point of the material used to form the barrier material, or else the barrier material may undergo undesirable melting during the 3D-printing process.

However, the melting point of the polymer used to form the injection molding guide should not be too low, or else when the molten polymer used to form the ring structure of the contraceptive device is added to the construct, the injection molding guide may become sufficiently warm that it will deform during the injection molding process. In one embodiment, the injection molding guide is a thermoplastic having a melting point above the temperature used for injection molding. In embodiments, the melting point of the polymer used to form the injection molding guide is greater than 110° C., or is greater than 120° C., or is greater than 130° C., or is greater than 140° C., or is greater than 150° C., or is greater than 160° C., or is greater than 170° C., or is greater than 180° C., or is greater than 190° C., or is greater than 200° C. In one embodiment, the injection molding guide is made from a cross-linked polymer, and thus does not have a melting or softening point. The cross-linked polymer may be formed by a thermosetting process, where two polyfunctional and inter-reactive reactants, e.g., reactive polymers, are combined and then caused to react with one another, such as by the addition of heat or a catalyst. In one aspect, the injection molding guide does not have a melting point or a softening point.

In one embodiment, the injection molding guide has a homogeneous composition throughout the structure of the guide. In other words, the guide has the same composition at every location of the guide. In one embodiment, the guide does not contain or comprise a coating, e.g., it does not have a sizing polymer. In one embodiment, the injection molding guide does not contain or comprise yarn or a multifilament thread. In one embodiment, the injection molding guide may be said to be non-fibrous. In one embodiment, the injection molding guide may be said to have a non-yielding or non-compressive surface, such that when pressure is applied to the surface, the surface does not move or yield or compress to any appreciable degree. In one embodiment, the injection molding guide is not formed from an elastomeric polymer, i.e., is non-elastomeric. In one embodiment, the injection molding guide may be described as non-porous.

In one embodiment, the injection molding guide has a uniform cross-section. In other words, the cross-section of the injection molding guide as viewed at any location along a diameter of the injection molding guide, has the same appearance. This feature is advantageous in that when the construct is placed within the mold prior to formation of the support ring, the pins that contact the surface of the injection molding guide may all be moved the same distance in order to contact a surface of the injection molding guide. When the injection molding guide has a non-uniform cross-section, then some pins may need to be moved further than other pins, in order for all pins to contact the surface of the injection molding guide.

Figure 6A:
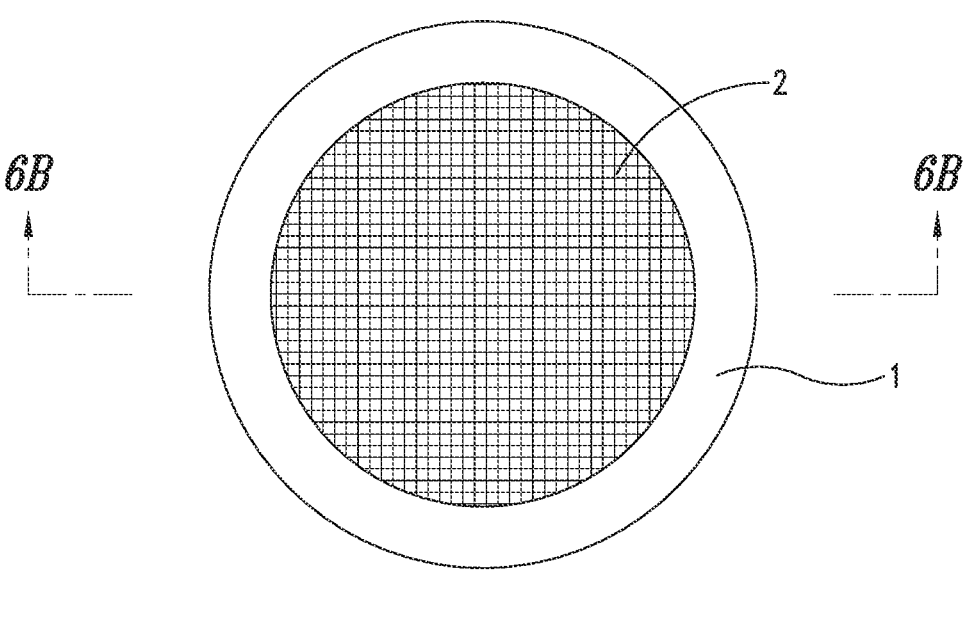
FIGS. 6A, 6B and 6C show schematics of an exemplary construct, where FIG. 6A provides a top view of the construct.
Figure 6B:
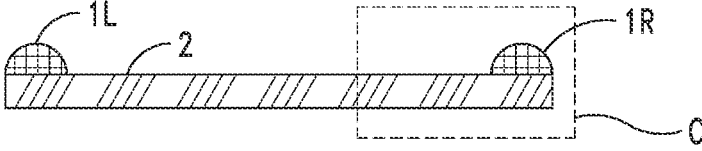
Figure 6C:
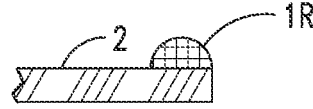

Exemplary partial cross sections of injection molding guides of the present disclosure are illustrated in FIG. 2, FIG. 3A through FIG. 3I, FIG. 4, FIG. 5A and FIG. 5B, where feature 1 is the injection molding guide and feature 2 is the porous barrier material. FIG. 6A provides a top view of a construct of the present disclosure that comprises an injection molding guide 1 and a porous barrier material 2. In one embodiment, the construct of the present disclosure consists of, or consists essentially of, an injection molding guide and a porous barrier material. FIG. 6A shows a line B that runs across the construct shown in FIG. 6A. When the construct of FIG. 6A is viewed in cross-section along the line B, the full cross-section of the construct is shown in FIG. 6B, which shows the porous barrier material 2 and two instances of the injection molding guide 1, which are labeled as IR and IL in FIG. 6B. When the construct of FIG. 6A is seen in partial cross section view, only one of the two instances of the injection molding guide 1 is seen, such as illustrated in the schematic of FIG. 6C, which is a portion of the cross sectional of the construct of FIG. 6A, and more specifically the portion encircled by the region C shown in FIG. 6C which shows the profile of the injection molding guide 1R.

When an injection molding guide is viewed in complete cross section at a location along a diameter of the injection molding guide, that complete cross section will show two shapes (see, e.g., features 1R and IL in FIG. 6B) separated by the inner diameter of the injection molding guide (see feature 2 in FIG. 6B), since the injection molding guide may have an annular shape and thus be in the form of a ring. For convenience, only one of those two shapes is shown in each of FIG. 2, FIG. 3A through FIG. 3I, FIG. 4, FIG. 5A, FIG. 5B and FIG. 6C, so that these figures show a partial cross-section of the injection molding guide and porous barrier material. When the injection molding guide is symmetrical in that it has a uniform cross section when viewed in complete cross section at a location along a diameter of the annular injection molding guide, that complete cross section will show two complementary shapes separated by a distance representative of the inner diameter of the annular injection molding guide, where those complementary shapes are identical in terms of appearance and size, regardless of which diameter of the injection molding guide is selected for the cross section. The complementary shapes may be the mirror images of one another, with the point of reflection being the center point of an annular injection molding guide, in other words, one shape (e.g., the hemisphere 1L in FIG. 6B) is the mirror image of the other shape (e.g., the hemisphere 1R in FIG. 6B). FIG. 6B shows a complete cross-section of the construct of FIG. 6A, while FIG. 6C shows a partial cross-section of the construct of FIG. 6A. A symmetrical injection molding guide may have a plane of symmetry, i.e, a plane may be drawn onto an image of the injection molding guide such that the plane cuts the injection molding guide image into two mirrored halves. A symmetrical injection molding guide may have a line of symmetry, i.e., an axis or imaginary line that passes through the center of the injection molding guide and divides it into identical halves, particularly when the injection molding guide is viewed from the top as in FIG. 1 or FIG. 6A.

As shown in FIG. 2, in one embodiment the injection molding guide may have an L-shaped cross-section. An L-shaped cross-section is advantageous in that it affords two planar surfaces which meet at a right angle to form a corner. When the construct is placed into a mold, and then pins are moved into contact with the injection molding guide, two surfaces of each pin may contact the injection molding guide when the injection molding guide has a corner formed from two planar surfaces. This option provides a particularly secure connection between the pins and the injection molding guide, thus lessening the chance that the construct will move while the polymer that forms the ring structure is injected into the mold. In aspects of the present disclosure, the injection molding guide comprises a plurality of planar surfaces, e.g., two, or at least two, three, or at least three, four, or at least four, five, or at least five, six or at least six planar surfaces. In one embodiment, the injection molding guide of the present disclosure comprises at least two planar surfaces which intersect, optionally at a right angle to form a corner.

FIG. 3 shows eight exemplary cross-sectional shapes for the injection molding guide of the present disclosure. In FIGS. 3A, 3B, 3G and 3H, the injection molding guide has an L-shaped cross-sectional shape. In FIGS. 3D, 3E and 3F, the injection molding guide as a T-shaped cross-sectional shape. In FIG. 3C, the injection molding guide has a U-shaped cross-sectional shape. Comparing FIGS. 3A and 3I, the injection molding guide has the same cross-sectional shape, however in FIG. 3A the outer edge of the injection molding guide coincides with the other edge of the barrier material, while in FIG. 3I, the outer edge of the barrier material extends beyond the outer edge of the injection molding guide. In an aspect, an injection molding guide can be placed such that it is flush with the external circumference of the barrier. In an aspect, an injection molding guide can be placed such that there is a spacing between the edge of an injection molding guide and the external circumference of the barrier.

Figure 3A:
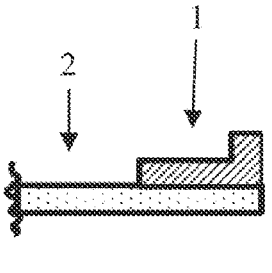
FIGS. 3A, 3B, 3C, 3D, 3E, 3F, 3G, 3H and 3I each show a cross-section of a portion of a schematic of an exemplary injection molding guide (1) provided on a porous barrier material (2) of an exemplary construct disclosed herein.
Figure 3B:
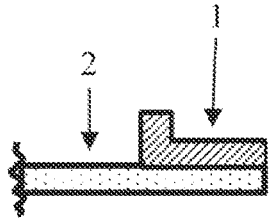
Figure 3C:
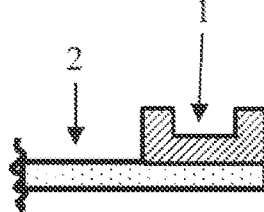
Figure 3D:
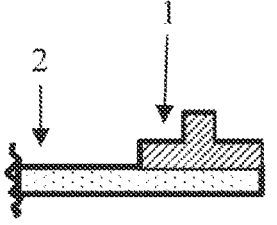
Figure 3E:
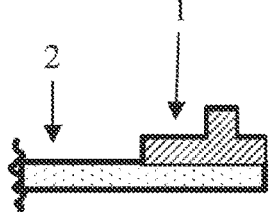
Figure 3F:
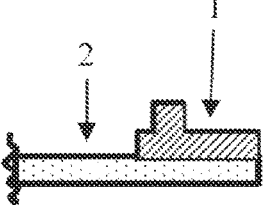
Figure 3G:
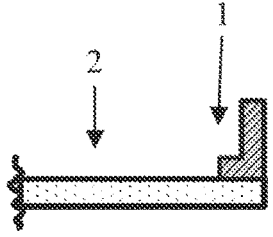
Figure 3H:
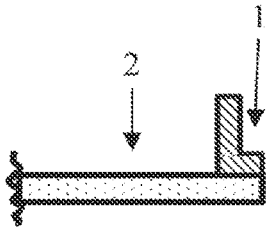
Figure 3I:
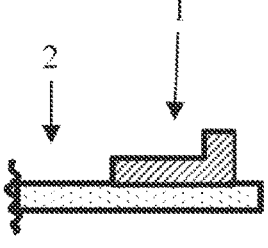

In each of the constructs shown in FIGS. 3A-3I, the injection molding guide has a plurality of planar surfaces. In FIG. 3A, the injection molding guide has six planar surfaces, two of which meet at a right angle to form one corner. In FIG. 3B, the injection molding guide has six planar surfaces, two of which meet at a right angle to form one corner. In FIG. 3C, the injection molding guide has eight planar surfaces, three of which meet at right angles to form two corners. In FIG. 3D, the injection molding guide has eight planar surfaces, four of which meet at right angles to form two corners. In FIG. 3E, the injection molding guide has eight planar surfaces, four of which meet at right angles to form two corners. In FIG. 3F, the injection molding guide has eight planar surfaces, four of which meet at right angles to form two corners. In FIG. 3G, the injection molding guide has six planar surfaces, two of which meet at a right angle to form one corner. In FIG. 3H, the injection molding guide has six planar surfaces, two of which meet at a right angle to form one corner. In FIG. 3I, the injection molding guide has six planar surfaces, two of which meet at a right angle to form a corner. The presence of a corner as a feature of an injection molding guide is useful because a pin may press against a corner of an injection molding device to provide enhanced stability of the construct within a mold. In one embodiment, the injection molding device has a base surface which is placed adjacent to the porous barrier material, where the base surface is a planar surface, and where the base surface may optionally not extend into the openings of the porous barrier material, as shown in FIG. 3A, FIG. 3B, FIG. 3C, FIG. 3D, FIG. 3E, FIG. 3F, FIG. 3G, FIG. 3H and FIG. 3I, although the base surface of any of the shapes shown in FIG. 3A, FIG. 3B, FIG. 3C, FIG. 3D, FIG. 3E, FIG. 3F, FIG. 3G, FIG. 3H and FIG. 3I may optionally extend into the porous barrier material.

In an aspect, an L-shaped injection molding guide can have the longer portion of the L-shape attached to the barrier as the base surface. In an aspect, an L-shaped injection molding guide can have the shorter portion of the L-shape attached to the barrier as the base surface. In an aspect with the longer portion of the L-shape attached to the barrier, the shorter portion of the L-shape can be closer to the exterior edge of the barrier. In an aspect with the longer portion of the L-shape attached to the barrier, the shorter portion of the L-shape can be closer to the interior portion of the barrier. In an aspect with the shorter portion of the L-shape attached to the barrier, the longer portion of the L-shape can be closer to the exterior edge of the barrier. In an aspect with the shorter portion of the L-shape attached to the barrier, the longer portion of the L-shape can be closer to the interior portion of the barrier. In an aspect, the L-shape of the L-shaped injection molding guide has two equally sized arms that join at a corner where one of these two arms provides the base surface.

In an aspect, the longer portion of an L-shape that is attached to the barrier, i.e., the base surface, has a length of about 2 mm to about 10 mm. In an aspect, the longer portion of an L-shape that is attached to the barrier has a length of about 3 to about 7 mm. In an aspect, the longer portion of the L-shape that is attached to the barrier has a height of about 0.2 to about 2 mm. In an aspect, the longer portion of the L-shape that is attached to the barrier has a height of about 0.3 to about 1 mm. In an aspect, the shorter portion of the L-shape has a height of about 0.2 to about 1.5 mm. In an aspect, the shorter portion of the L-shape has a height of about 0.3 to about 1 mm. In an aspect, the shorter portion of the L-shape has a width of about 0.5 to about 4 mm. In an aspect, the shorter portion of the L-shape has a height of about 0.7 to about 2.5 mm. In an aspect, the L-shape of the L-shaped injection molding guide has two equal portions that join at a corner, where each portion has a length of about 2 mm to about 10 mm.

The construct and contraceptive device of the present disclosure each includes a barrier material and an injection molding guide. As mentioned previously, in an aspect, an injection molding guide can be attached to the barrier on only one side. However, in another aspect, an injection molding guide can be attached to both sides of the barrier material. This later aspect is illustrated in FIG. 4. FIG. 4 shows a schematic of an exemplary injection molding guide (1) provided on a barrier material (2) of an exemplary contraceptive medical device disclosed herein, where the injection molding guide (1) is affixed to each of the top and the bottom of the barrier material.

In an aspect, the injection molding guide has a corner formed by intersection of two planar surfaces. Optionally, the injection molding guide has a corner formed by two planar surfaces intersecting one another, for example to form an angle of about 45 degrees to about 135 degrees, or about 80 degrees to about 100 degrees, e.g., at an angle of 85-90 degrees, or at about a 90 degree angle. Thus, as discussed above, the injection molding guide of the present disclosure may include a corner, where two planar surfaces meet at a right angle. However, in an aspect, the injection molding guide of the present disclosure may have two planar surfaces that meet to form an angle other than an about 90 degree angle. For example, as shown in FIG. 5A and FIG. 5B, an injection molding guide of the present disclosure may include two planar surfaces that intersect to form an angle that is greater than 90 degrees, for example, 100 degrees, or more than 100 degrees. In one aspect, the two planar surfaces intersect to form an angle that is less than 90 degrees, for example, about 45 degrees.

As illustrated in the set of figures FIG. 6A, FIG. 6B and FIG. 6C, the injection molding guide need not have only planar surfaces. As illustrated in the set of figures FIG. 6A, FIG. 6B and FIG. 6C, the injection molding guide may have a curved surface, as shown by the profile of features 1R and 1L in FIG. 6B and FIG. 6C. The curved surface of the injection molding guide may engage the pins of an injection molding machine in a uniform manner when the injection molding guide is symmetrical as shown in FIG. 6BA. Thus, in one aspect, the present disclosure provides a contraceptive device comprising a polymeric ring, a porous barrier material and an injection molding guide, the injection molding guide being symmetrical in cross-section, and where both of the injection molding guide and the porous barrier material are at least partially embedded within the polymeric ring.

In an aspect, the injection molding guide may be described as an annular ring, having an inner diameter and an outer diameter. In an aspect, the inner diameter of an injection molding guide is about 42 mm to about 46 mm. In an aspect, the outer diameter of an injection molding guide is about 45 mm to about 53 mm. In an aspect, the injection molding guide may be non-circular. The barrier mesh may be rectangular, square, pentagonal, hexagonal, heptagonal or octagonal.

An injection molding guide can comprise one or more polymer as described herein. In an aspect, an injection molding guide can comprise an absorbable polymer. In another aspect, an injection molding guide can comprise a non-degradable polymer. In an aspect, an injection molding guide comprises an absorbable polymer that comprises greater than 70% (w/w) lactide residues. In an aspect, the injection molding guide comprises an absorbable polymer that comprises greater than 80% (w/w) lactide residues.

In an aspect, an injection molding guide comprises an absorbable polymer that comprises about 70% (w/w) to about 90% (w/w) lactide residues and 10% (w/w) to 30% (w/w) trimethylene carbonate residues. In an aspect, an injection molding guide comprises an absorbable polymer that comprises greater than 80% (w/w) lactide residues and also contains trimethylene carbonate residues. In an aspect, the disclosure provides an injection molding guide that is 3D-printed onto a mesh that comprises an absorbable polymer that comprises greater than 75% (w/w) lactide residues. In an aspect, the disclosure provides an injection molding guide that has a L-shaped cross-section and is attached such that the exterior edge of an injection molding guide and the outer circumference of the mesh are flush.

In an aspect, the barrier material and the injection molding guide can both comprise an absorbable polymer. In an aspect, the barrier material and the injection molding guide can both comprise a non-absorbable polymer. In an aspect, the barrier can comprise an absorbable polymer and the injection molding guide can comprise a non-absorbable polymer. In an aspect, the barrier can comprise a non-absorbable polymer and the injection molding guide can comprise an absorbable polymer.

In an aspect, the injection molding guide comprises polypropylene that is 3D-printed onto a barrier material that comprises polypropylene. The injection molding guide has an L-shaped cross-section and is attached to the barrier material such that the exterior edge of an injection molding guide and the outer circumference of the barrier material are flush. In an aspect, the barrier material comprises a knitted polypropylene mesh.

In an aspect, the injection molding guide comprises an absorbable polymer that comprises greater than 80% (w/w) lactide residues, and that injection molding guide is 3D-printed onto a barrier material in the form of a mesh that also comprises an absorbable polymer that comprises greater than 80% (w/w) lactide residues. Optionally, the injection molding guide has a L-shaped cross-section and is attached to the barrier material such that the exterior edge of the injection molding guide and the outer circumference of the mesh are flush.

In an aspect, the injection molding guide comprises an absorbable polymer that comprises about 70% (w/w) to about 90% (w/w) lactide residues and 10% (w/w) to 30% (w/w) trimethylene carbonate residues. Such an injection molding guide is optionally 3D-printed onto a barrier material in the form of a mesh that comprises an absorbable polymer that comprises greater than 75% (w/w) lactide residues. Optionally, the injection molding guide has a L-shaped cross-section and is attached to the barrier material such that the exterior edge of an injection molding guide and the outer circumference of the mesh are flush.

Polymeric Ring

A contraceptive device of the present discloses comprises a polymeric ring that encircles the outer edge of a barrier material. The polymeric ring is formed from a polymeric material, sometimes referred to herein as the matrix. Suitable polymers for the matrix include, without limitation, polyethylene vinyl acetate, polyurethane and silicone.

The polyurethane polymer used as the matrix can include but is not limited to a polyether urethane, a silicone-polycarbonate-urethane (TSPCU), a silicone-polyether-urethane (TSPU), a polycarbonate-urethane and a segmented polyurethane.

The polyethylene vinyl acetate polymer used as the matrix may optionally have a vinyl acetate content of about 15% (w/w) to about 50% (w/w). Polyethylene vinyl acetate polymers that can be used include but are not limited to polymers that contain about 16% to about 20% vinyl acetate, about 25% to about 35% vinyl acetate and about 35% to about 50% vinyl acetate. Commercially available polyethylene vinyl acetate polymer that can be used include but are not limited to Evatane 18-150 (Arkema, France), Evatane 28-40 (Arkema, France) and Evatane 38-41 (Arkema, France).

The silicone that can be used to form the ring component can be formed from a two-part silicone composition. In one aspect, the silicone that is used to manufacture the ring component is a polysiloxane. The polysiloxane has the general structure —[Si(R2)-O]— where R can include but is not limited to hydrogen, methyl, ethyl, phenyl, vinyl, trifluoropropyl or a combination thereof. The polysiloxane can be a linear polymer, a branched polymer, or a combination thereof. In an aspect, a two-part liquid silicone rubber can be used to manufacture the ring component. The two-part silicone composition can be mixed together and can be cured or crosslinked using addition curing, condensation curing or a combination thereof. By selecting the appropriate compositions, certain polysiloxanes can be cured at about 20° C. to about 50° C. This is generally called room temperature vulcanization. Certain polysiloxane compositions can be cured at about 51° C. to about 130° C. This is generally called low temperature vulcanization. Certain polysiloxane compositions can be cured above 130° C. This is generally called high temperature vulcanization. The components of the two-part composition or mixture may be referred to as heat-curable in the case where they are cured or crosslinked by application of elevated temperature. Addition curing compositions can include a platinum catalyst or a peroxide compound to facilitate curing of the specific polysiloxane formulations.

Peroxide compounds that can be used include but are not limited to dicumyl peroxide, benzoyl peroxide, 2,4-dichlorobenzoyl peroxide, dibenzoylperoxide, 2,5-dimethyl-2,5-di-t-butylperoxyhexane or a combination thereof.

In an aspect the one part of a two-part silicone composition which are used to form the ring structure can comprise vinyl groups. In an aspect the second part of the two-part composition can comprises hydride groups.

Silicones that can be used to manufacture the ring component include but are not limited to Silastic® Q7-4535, Silastic® Q7-4550, Silastic® Q7-4565, Silastic® Q7-4720, Silastic® Q7-4735, Silastic® Q7-4750, Silastic® Q7-4765, Silastic® Q7-4780, Silastic® C6-135, Silastic® C6-150, Silastic® C6-165, Silastic® C6-180, Silastic® C6-350, Silastic® 7-6830, Silastic® Q7-4840, Silastic® Q7-4850, Silastic® Q7-4750, Silastic® 7-6840, Silastic® 7-4860, Silastic® 7-6860, Silastic® 7-4870, Dow Corning® C6-530, Dow Corning® C6-540, Dow Corning® C6-550, Dow Corning® C6-560, Dow Corning® C6-570 and the Silbione® Biomedical Silicones (Elkem). In an aspect, the silicone used is Silastic® Q7-4840. In an aspect, the silicone used is Silastic® Q7-4850. In an aspect, the silicone used is LSR M140.

Copolymers of silicone can also be used. Examples of such polymers include poly(dimethyl siloxane)-containing block copolymers, poly(dimethyl siloxane)-block-poly(ethylene glycol), poly(dimethyl siloxane)-block-poly(vinyl alcohol), poly(dimethyl siloxane)-block-poly(acrylic acid), poly(2-hydroxyethyl methacrylate-g-dimethylsiloxane), poly(2,3-dihydroxypropyl methacrylate-g-dimethylsiloxane), poly(dimethylacrylamide)-block-poly(dimethyl siloxane)-block-poly(dimethylacrylamide, poly(dimethyl siloxane)-block-poly(2-(dimethylamino)ethyl acrylate).

The silicones used to form the ring structure may be cured to form an elastomeric ring component. The curing temperatures and curing times will vary depending on the specific silicone formulation used. For example, the curing temperature may vary between room temperature (15 to 25° C.) and 150° C. In an aspect, the curing temperature is within the range 85 to 140° C. In a preferred aspect, the curing temperature is in the 110 to 135° C. range. The curing time may vary between a few seconds and several hours, depending on the specific silicone formulation used and the curing temperature used. In an aspect, the curing time is in the range of 1 minute to 5 hrs. In an aspect, the curing time is in the range of 1 to 5 minutes. In an aspect, the curing time is in the range of 1 to 5 minutes and the curing temperature is in the range of 115 to 140° C.

The hardness of the ring structure can be measured on the standard Shore scale, using a durometer. The ring may have a durometer of about Shore A 20 to about shore A 80. In an aspect, the ring durometer is Shore A 30 to Shore A 60. In another aspect, the ring durometer is Shore A 40 to Shore A 50. In another aspect, the ring durometer is Shore A 40 to Shore A 46.

The ring component has an inner diameter and an outer diameter. The inner diameter can be about 35 mm to about 50 mm. In an aspect, the inner diameter can be about 38 mm to about 45 mm. In an aspect, the inner diameter can be about 38 mm to about 42 mm. In one aspect, the ring component has an inner diameter of about 40 mm. In another aspect, the ring component has an inner diameter of about 35 mm, about 36 mm, about 37 mm, about 38 mm, about 39 mm, about 41 mm, about 42 mm, about 43 mm, about 44 mm, about 45 mm or about 46 mm.

The outer diameter can be about 45 mm to about 70 mm. In an aspect, the outer diameter can be about 45 mm to about 65 mm. In an aspect, the outer diameter can be about 52 mm to about 58 mm.

In an aspect, the ring component has an outer diameter of about 55 mm. In another aspect, the ring component has an outer diameter of about 50 mm, about 51 mm, about 52 mm, about 53 mm, about 54 mm, about 56 mm, about 57 mm, about 58 mm, about 59 mm or about 60 mm.

In one aspect, the ring component has a rounded outer edge and a rounded inner edge. The rounded outer edge of the ring component can have a radius of about 1.5 mm to about 3.0 mm. In an aspect, the rounded outer edge of the ring component can have a radius of about 1.8 mm to about 2.2 mm. The rounded inner edge of the ring component can have a radius of about 1.8 mm to about 3.5 mm. In an aspect, the rounded inner edge of the ring component can have a radius of about 2.2 mm to about 2.8 mm Absorbable and Non-Absorbable Polymers In one aspect, one or more of the barrier material, injection molding guide and/or the ring structure is formed from a non-absorbable polymer. The term non-absorbable polymer as used herein, refers to a polymer that is completely or substantially incapable of being broken down and absorbed, either fully or partially, by tissue after introduction into a living subject. Non-absorbable polymers are referred to herein as non-absorbable, non-bioabsorbable, non-biostable, non-bioresorbable, non-biodegradable, non-resorbable, non-degradable, not soluble, not bioerodible, or not naturally dissolving. Each of these terms may be used interchangeably.

For example, one or more non-absorbable polymers may be used to form fibers that may be used to form the barrier material. The barrier material may have a mesh structure, where the mesh may be formed from non-absorbable polymers. The barrier material may be a film that is formed from non-absorbable polymers. Any non-absorbable polymer that is able to be formed into a flexible fiber that can be manufactured into a mesh can be used.

Examples of non-absorbable polymers include, but are not limited to polyolefins, polyesters, polyamides, polyurethanes, and fluoropolymers. Polyolefins can include but are not limited to polyethylene, polypropylene and copolymers thereof. Non-absorbable polyester can include but is not limited to polyethylene terephthalate (PET) and poly-1,4-cyclohexylene-dimethylene terephthalate (PCDT). Non-absorbable polyamides can include but are not limited to nylon 6, nylon 66, nylon 4, nylon 11, nylon 6,10 and aramid (e.g. Nomex and Kevlar). Non-absorbable polyurethanes can include but are not limited to Spandex, lycra, polycarbonate-urethanes, silicone-polycarbonate-urethanes, polyether-urethane, silicone-polyether-urethane. Non-absorbable fluoropolymers can include but are not limited to polytetrafluoroethylene (PTFE) such as that sold under the registered trademark TEFLON™ E.I. DuPont de Nemours & Co., expanded PTFE (ePTFE) and polyvinylidene fluoride. Other non-absorbable polymers suitable for use in the present disclosure include polyetheretherketone (PEEK), polyimide, polyacrylonitrile, acrylonitrile-vinyl acetate copolymers, acrylonitrile-methyl acrylate copolymers, acrylonitrile-vinyl chloride copolymers, acrylonitrile-vinylidene chloride copolymers, regenerated cellulose (e.g. Rayon®), polysulfone, fiberglass, acrylic polymers. In one embodiment, the non-absorbable polymer is medically acceptable in that the polymer will not cause an adverse reaction when the polymer is positioned within a subject's body. In one embodiment, the non-absorbable polymer is polyethylene. In another embodiment, the non-absorbable polymer is polypropylene.

Any absorbable polymer that can be used for the construction of the fibers, mesh, and films can be used to manufacture the barrier material for the contraceptive device. As used herein, a polymer that degrades, either fully or partially, after being placed into a host may be referred to herein as absorbable, bioabsorbable, bioresorbable, biodegradable, resorbable, naturally dissolving, erodible or bioerodable, soluble or biosoluble. Each of these terms may be used interchangeably with another. Absorbable polymers that can be used include polyesters, polycarbonates, polyester-carbonates, polyurethanes, polyamides, polyether-esters, polyorthoesters, polyanhydrides, silk, and combinations thereof.

In one aspect, one or more of the barrier material, injection molding guide and/or the ring structure is formed from an absorbable polymer. Suitable absorbable polymers include polymers resulting from the polymerization of at least one monomer selected from the group of glycolide, lactide, ε-caprolactone, trimethylene carbonate, p-dioxanone, 1,5-dioxepan-2-one and morpholinedione. The polymerization of these monomers can be initiated by an initiator compound having a single initiator group, two initiator groups, three initiator groups, four initiator groups or more than four initiator groups. Initiator groups that can be used include but are not limited to hydroxyl groups, amine groups and thiol groups. Initiators with a single initiator group include any compound with a single hydroxyl. Examples of single hydroxyl alcohols include aliphatic and aromatic alcohols. Examples of alcohols include but are not limited to methanol, octanol, nonanol, decanol, dodecanol glycolic acid, lactic acid and methoxy polyethylene glycol. Initiators with a single initiator group include any compound with a single amine Examples of single amine compounds include aliphatic and aromatic amines Examples of amines include but are not limited to triethylamine, ethyldiisopropylamine, dibutylamine, tributylamine, trioctylamine, and 4-(N, N-dimethyl)aminopyridine. Initiators with two initiator groups include diols and diamines. Diols include aliphatic and aromatic diols. Examples of diols include but are not limited to propanediol, butanediol, hexanediol, dodecanediol, octanediol, decanediol, and polyethylene glycol. Initiators with three functional groups include but are not limited to glycerol, trimethylolpropane, triethanolamine, N-2-aminoethyl-1,3-propanediamine, 1,1,1-tris(hydroxymethyl)ethane, and pentaerythritol monostearate. Initiators used to produce polymers with 4 or more arms can include but are not limited to pentaerythritol, glucose and dipentaerythritol.

Polyaxial polymers that can be used to manufacture the barrier material of the contraceptive device are described in U.S. Pat. Nos. 6,462,169, 6,794,485, 7,129,319 and 7,070,858, each of which is herein incorporated in its entirety.

Catalysts that can be used to manufacture polyester polymers include but are not limited to a tin based catalyst, aluminum-based catalysts, zinc based catalyst and a bismuth based catalyst. Tin-based catalysts that can be used include but are not limited to tin (II) 2-ethylhexanoate. Aluminum based catalysts that can be used include but are not limited to aluminum isopropoxide, and triethyl aluminum, zinc based catalysts that can be used include but are not limited to zinc lactate and bismuth based catalysts that can be used include but are not limited to bismuth subsalicylate In another aspect, the absorbable polymers can be random copolymers or block copolymers. Random copolymers can be manufactured by adding 2 or more different monomers to the reaction mixture and allowing the mixture to polymerize. Block copolymers can be manufactured by first adding one or more monomers and allowing the monomers to polymerize and then adding a second monomer that is different from at least one of the first monomers, to the initial polymer and then allowing that to polymerize further. The resultant polymer will thus have a block of similar units linked to a block of similar units that are different from the first units.

In one aspect, the absorbable polymer can comprise 50% (w/w) or greater lactide residues. In another aspect the absorbable polymer can comprise 60% (w/w) or greater lactide residues. In another aspect, the absorbable polymer can comprise 70% (w/w) or greater lactide residues. In another aspect, the absorbable polymer can comprise 80% (w/w) or greater lactide residues. Such absorbable polymers having 50% or more (w/w) lactide residues may be referred to herein as lactide polymers or lactide copolymers.

The lactide polymer may also contains residues from the polymerization of glycolide, ε-caprolactone, trimethylene carbonate, p-dioxanone, 1,5-dioxepan-2-one and/or morpholinedione. In one aspect, the absorbable lactide polymer contains trimethylene carbonate residues. In another aspect, the lactide polymer contains a block of trimethylene carbonate residues and a block of lactide residues. In one aspect, the lactide polymer can be manufactured with an added lactide to trimethylene carbonate ratio of 88:12 (molar ratio).

Referring to the manufacture of absorbable polymers, in one aspect, the initiator used for the polymerization is a hydroxyl based initiator. In one aspect, the initiator is a diol. In another aspect, the initiator is 1,3 propanediol. In one aspect, the 1,3 propanediol is used to initiate polymerization of trimethylene carbonate. In one aspect, the initiator is a triol. In another aspect, the initiator is trimethylolpropane. In one aspect, the trimethylolpropane is used to initiate polymerization of trimethylene carbonate. Once the polymerization has essentially completed, lactide is added to the reaction mixture to produce a triaxial or linear polymer with a trimethylene carbonate based core that is terminated with a block of polylactide.

In another aspect, the absorbable polymer comprises polydioxanone residues.

In another aspect, the absorbable polymer comprises polylactic acid. The polylactic acid can be synthesized from L-lactide, D-lactide, D,L-lactide or a combination thereof.

Still referring to the absorbable polymer, in one aspect, the absorbable polymer comprises a copolymer of residues of lactide, trimethylene carbonate and ε-caprolactone. In one aspect, the copolymer is a block copolymer. In one aspect, the block copolymer has one block of trimethylene carbonate residues and a second block comprising residues of lactide and ε-caprolactone residues. In one aspect, the copolymer can be manufactured with an added lactide monomer of at least 70% of the total weight of all added monomers. In a preferred aspect, the added lactide monomer is between 70% and 90% of the total weight of all added monomers. In one aspect, the copolymer can be manufactured with an added TMC monomer of at least 10% of the total weight of all added monomers. In a preferred aspect, the added TMC monomer is between 10% and 20% of the total weight of all added monomers. In one aspect, the copolymer can be manufactured with an added ε-caprolactone monomer of at least 3% of the total weight of all added monomers. In a preferred aspect, the added ε-caprolactone monomer is between 3% and 15% of the total weight of all added monomers. In one aspect, the initiator used for the polymerization is a hydroxyl based initiator. In one aspect, the initiator is a diol. In another aspect, the initiator is 1,3 propanediol. In one aspect, the 1,3 propanediol is used to initiate polymerization of trimethylene carbonate. In one aspect, the initiator is a triol. In another aspect, the initiator is trimethylolpropane. In one aspect, the trimethylolpropane is used to initiate polymerization of trimethylene carbonate. Once the polymerization has essentially completed, lactide and ε-caprolactone may be added to the reaction mixture to produce a triaxial or linear polymer with a poly(trimethylene carbonate) based core that is terminated with a block of lactide-co-caprolactone copolymer.

Still referring to the absorbable polymer, in one aspect, the polymer comprises a copolymer of residues of glycolide, trimethylene carbonate and ε-caprolactone. In one aspect, the copolymer is a block copolymer. In one aspect, the block copolymer has one block of trimethylene carbonate residues and a second block comprising residues of glycolide and ε-caprolactone. In one aspect, the copolymer can be manufactured with an added glycolide monomer of at least 45% of the total weight of all added monomers. In a preferred aspect, the added glycolide monomer is between 45% and 65% of the total weight of all added monomers. In one aspect, the copolymer can be manufactured with an added TMC monomer of at least 20% of the total weight of all added monomers. In a preferred aspect, the added TMC monomer is between 20% and 30% of the total weight of all added monomers. In one aspect, the copolymer can be manufactured with an added ε-caprolactone monomer of at least 15% of the total weight of all added monomers. In a preferred aspect, the added ε-caprolactone monomer is between 15% and 30% of the total weight of all added monomers. In one aspect, the initiator used for the polymerization is a hydroxyl based initiator. In one aspect, the initiator is a triol. In another aspect, the initiator is trimethylolpropane. In one aspect, the trimethylolpropane is used to initiate a polymerization of monomers minimally comprising trimethylene carbonate. Once the polymerization has essentially completed, monomers minimally comprising glycolide are added to the reaction mixture to produce a triaxial polymer with a trimethylene carbonate based core that is terminated with a homopolymer or copolymer block of a glycolide-based end graft.

Still referring to the absorbable polymer, in one aspect, the polymer comprises a copolymer of residues of lactide, trimethylene carbonate and ε-caprolactone. Optionally, the polymer may include glycolide. In one aspect, the copolymer is a block copolymer. In one aspect, the block copolymer has one block of poly(trimethylene carbonate) and a second block comprising residues of lactide. In one aspect, the copolymer can be manufactured with an added lactide monomer of at least 35% of the total weight of all added monomers. In a preferred aspect, the added lactide monomer is between 30% and 45% of the total weight of all added monomers. In one aspect, the copolymer can be manufactured with an added TMC monomer of at least 10% of the total weight of all added monomers. In a preferred aspect, the added TMC monomer is between 10% and 40% of the total weight of all added monomers. In one aspect, the copolymer can be manufactured with an added ε-caprolactone monomer of at least 30% of the total weight of all added monomers. In a preferred aspect, the added ε-caprolactone monomer is between 30% and 40% of the total weight of all added monomers. In one aspect, the initiator used for the polymerization is a hydroxyl based initiator. In one aspect, the initiator is a triol. In another aspect, the initiator is trimethylolpropane or triethanolamine. In one aspect, the trimethanolamine is used to initiate a polymerization of monomers minimally comprising trimethylene carbonate. Once the polymerization has essentially completed, monomers minimally comprising lactide are added to the reaction mixture to produce a triaxial polymer with a poly(trimethylene carbonate) based core that is terminated with a homopolymer or copolymer block of a lactide-based end graft.

Absorbable polyesters include polyhydroxyalkanoates. Examples of suitable polyhydroxyalkanoates include but are not limited to poly(3-hydroxybutyrate) (PHB), poly(3-hydroxybutyrate-co-3-hydroxyvalerate) (PHBV), poly(3-hydroxybutyrate-co-4-hydroxybutyrate) (P(3HB-co-4HB)), poly[3-hydroxybutyrate-co-3-hydroxyhexanoate] (P(3HB-co-3HH)), and poly[(R)-4-hydroxybutyrate] poly(4-hydroxybutyrate) (P(4HB).

In an aspect, a barrier construct comprises the barrier material and an injection molding guide.

Biologically Active Agent

The ring structure may comprise a biologically active agent. The biologically active agent may be an agent that has spermicidal activity, a hormone, antimicrobial, antibacterial agents, antifungal agents, antiprotozoal agents, antiviral agents and mixtures thereof. In one aspect, the ring structure comprises a composition that is spermicidal. In another aspect, the ring structure comprises a hormone. In another aspect, the ring structure comprises an antimicrobial agent. In another aspect, the ring structure comprises an antibacterial agent. In another aspect, the ring structure comprises an antifungal agent. In another aspect, the ring structure comprises an antiprotozoal agent. In another aspect, the ring structure comprises an antiviral agent. Optionally, the ring structure comprises two of these agents, e.g., a spermicidal agent and a hormone.

Agents that exhibit spermicidal activity include but are not limited to nonoxynol-9, octoxynol-9, benzalkonium chloride, sodium cholate, copper, a ferrous compound and a ferrous compound in combination with ascorbic acid. Ferrous compounds that can be used include ferrous gluconate, ferrous sulfate, ferrous chloride, ferrous fumarate, ferrous lactate, ferrous acetate, ferrous oxalate, ferrous ascorbate, combinations thereof as well as hydrates thereof.

Hormonal agents include but are not limited to levonorgestrel, ethinyl estradiol, 170 estradiol, nomegestrol acetate, etonogestrel, progesterone, nestorone, norethisterone enanthate, medroxyprogesterone acetate, and estradiol cypionate.

Antiviral agents include but are not limited to Acyclovir, Brivudine, Cidofovir, Curcumin, Dapirivine, Desciclovir, 1-Docosanol, Edoxudine, Frameyclovir, Fiacitabine, Ibacitabine, Imiquimod, Lamivudine, Penciclovir, Valacyclovir, Valganciclovir and salts or esters thereof. Curcumin, Acyclovir, Famcyclovir, Dapirivine and Valacyclovir are preferred antiviral agents.

Antifungal agents include but are not limited to Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid and salts or esters thereof.

Antibacterial agents include but are not limited to Acrosoxacin, Amifloxacin, Amoxycillin, Ampicillin, Aspoxicillin, Azidocillin, Azithromycin, Aztreonam, Balofloxacin, Benzylpenicillin, Biapenem, Brodimoprim, Cefaclor, Cefadroxil, Cefatrizine, Cefcapene, Cefdinir, Cefetamet, Cefinetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Timidazole, Tosufloxacin, Trimethoprim and salts or esters thereof.

Antiprotozoal agents include but are not limited to Acetarsol, Azanidazole, Chloroquine, Metronidazole, Nifuratel, Nimorazole, Omidazole, Propenidazole, Secnidazole, Sineflngin, Tenonitrozole, Temidazole, Timidazole and salts or esters thereof.

The initial loading of the biologically active agent into the ring structure is between about 1% (w/w) to about 50% (w/w). In an aspect, the initial loading of the biologically active agent into the ring structure is between about 5% (w/w) to about 30% (w/w). In an aspect the initial loading of the biologically active agent into the ring structure is between about 5% (w/w) to about 15% (w/w).

The contraceptive device, and in particular the ring structure, can comprise a ferrous compound and ascorbic acid. In an aspect, the contraceptive device can comprise ferrous gluconate and ascorbic acid. In an aspect, the contraceptive device can comprise ferrous gluconate dihydrate and ascorbic acid. In an aspect, the loading of the ferrous gluconate dihydrate is between about 5% (w/w) and about 15% (w/w). In an aspect, the loading of the ferrous gluconate dihydrate is between about 5% (w/w) and about 15% (w/w) and the loading of ascorbic acid is between 4% (w/w) and about 12% (w/w). In an aspect, the contraceptive device has a molar ratio of ascorbic acid to ferrous gluconate dihydrate of greater than 1, greater than 1.5, greater than 1.8 and greater than 2.

In an aspect, the contraceptive device, and in particular the ring structure, can comprise between about 400 mg and 1000 mg ferrous gluconate dihydrate. In an aspect, the contraceptive device can comprise between about 400 mg and 700 mg ferrous gluconate dihydrate. In another aspect, the contraceptive device can comprise between about 450 mg and 550 mg ferrous gluconate dihydrate. In an aspect, the contraceptive device can comprise between about 400 mg and 700 mg ferrous gluconate dihydrate and between 250 mg and 500 mg ascorbic acid. In another aspect, the contraceptive device can comprise between about 450 mg and 550 mg ferrous gluconate dihydrate and between about 350 mg to about 450 mg ascorbic acid.

The contraceptive device can comprise one or more excipients. An excipient can function to modulate the pH of the immediate local environment in which the contraceptive device is placed, to mediate the acidity of the initial eluate from the device, to interact with the vaginal mucus to increase mucus viscosity, to act as an anti-oxidant, to act as a preservative or to modulate the release of the biologically active compounds.

Compounds that modulate the pH of the immediate local environment, include but are not limited to acids such as ascorbic acid, oxalic, citric, tartaric, malic, maleic acid, lactic acid and glycolic acids, poly-amino and polycarboxylic acid mixtures such as ampholines, amino acids such as glycine, alanine, asparagine, aspartic acid, cysteine, glutamic acid, glutamine, arginine, histidine, isoleucine, leucine, lysine, methionine, phenylanaline, proline, serine, threonine, tryptophan, tyrosine, and valine, and polyacids that release acidic compounds upon degradation, such as polyglycolic acid, carboxyl-bearing polyglycolide, poly(lactide-co-glycolide), and poly(glycolide-co-trimethylene carbonate, glycolic acid diblock copolymers such as methoxypolyethylene glycol-polyglycolide, and glycolic acid triblock copolymers such as polyglycolide-polyethylene glycol-polyglycolide. The loading of a compound that can modulate pH is between about 1% (w/w) to about 20%. In an aspect, the loading of a compound that can modulate pH is between about 2% (w/w) to about 10%. In an aspect, the loading of a compound that can modulate pH is between about 2% (w/w) to about 6% (w/w).

Compounds that mediate the acidity of the initial eluate from the device include but are not limited to amino acids such as glycine, alanine, asparagine, aspartic acid, cysteine, glutamic acid, glutamine, arginine, histidine, isoleucine, leucine, lysine, methionine, phenylanaline, proline, serine, threonine, tryptophan, tyrosine, and valine, phosphate salts such as sodium dihydrogen phosphate, sodium hydrogen phosphate, trisodium phosphate and hydrates thereof, sodium carbonate, sodium acetate and sodium bicarbonate. The loading of a compound that can modulate the acidity of the initial eluate is between about 1% (w/w) to about 20%. In an aspect, the loading of a compound that can modulate the acidity of the initial eluate is between about 2% (w/w) to about 10% (w/w). In an aspect, the loading of a compound that can modulate the acidity of the initial eluate is between about 2% (w/w) to about 6% (w/w).

Compounds that act as anti-oxidants, include but are not limited to ascorbic acid, sodium ascorbate, calcium ascorbate, magnesium ascorbate, alpha-tocopherol or vitamin E, glutathione, lipoic acid, uric acid, Beta-carotene, retinol, ascorbyl palmitate, butylated hydoxyanisole, butylated hydroxytoluene, dihydroxybenzoic acid, and propyl gallate. The loading of an anti-oxidant compound is between about 0.5% (w/w) to about 20%. In an aspect, the loading of an anti-oxidant compound is between about 1% (w/w) to about 10% (w/w). In an aspect, the loading of a compound that can modulate the acidity of the initial eluate is between about 1% (w/w) to about 6% (w/w).

Compounds that act as preservatives include but are not limited to benzyl alcohol, benzalkonium chloride, butyl paraben, chorobaraben, meta cresol, chlorocresol, methyl paraben, phenyl ethyl alcohol, propyl paraben, phenol, benzoic acid, sorbic acid, sodium benzoate and bronidol. The loading of a preservative is between about 0.05% (w/w) to about 5%. In an aspect, the loading of a preservative is between about 0.1% (w/w) to about 2% (w/w). In an aspect, the loading of a preservative is between about 0.1% (w/w) to about 1% (w/w).

Compounds that can act as release modifying agents include degradable polymers, sucrose, sodium chloride, and dextrose. Degradable polymers that can be used include but are not limited to a polyester that is derived from cyclic monomers selected from the group consisting of lactides, glycolide, epsilon-caprolactone, trimethylene carbonate, and para-dioxanone, and combinations thereof. Additionally, the polyester can be synthesized with acid end groups. For instance, glycolic acid can be used as an initiator during synthesis of low molecular weight polymers to provide the acid end groups. The polyester can be formed by ring opening polymerization of acid-bearing hydroxylic initiators such as glycolic, lactic, malic, tartaric, and citric acid to provide the polymer with acidic end groups. The polyester can be processed by grinding the material into a fine powder to create the microparticulates. The particulates can then be incorporated into the ring formulation prior to forming the ring component.

In an aspect, the polyester is a polyglycolic acid. In an aspect, the polyester is a polyglycolic acid, the ring opening polymerization of which is initiated using glycolic acid. In an aspect the polyglycolic acid is micronized to form particles of polyglycolic acid. In an aspect, the polyglycolic acid particles have a mean diameter (volume weight) of less than 20 µm, less than 15 µm, less than 10 µm, less than 8 µm or less than 5 µm.

In an aspect, the polyester is a poly(glycolic acid-co-lactic acid) copolymer. In an aspect, the polyester is a poly (glycolic acid-co-lactic acid) copolymer, the ring opening polymerization of which is initiated using glycolic acid. In an aspect the poly(glycolic acid-co-lactic acid) copolymer is micronized to form particles of poly(glycolic acid-co-lactic acid) copolymer. In an aspect, the poly(glycolic acid-co-lactic acid) copolymer particles have a mean diameter (volume weight) of less than 20 µm, less than 15 µm, less than 10 µm, less than 8 µm or less than 5 µm.

In an aspect, the release modifying agent can increase the amount in milligrams of biologically active agent released from the contraceptive device into simulated vaginal fluid by greater than 1.1 over a seven-day sampling period as compared to the contraceptive device without the release modifying agent.

In an aspect, the release modifying agent can increase the amount in milligrams of biologically active agent released from the contraceptive device into simulated vaginal fluid by greater than 1.5 over a seven-day sampling period as compared to the contraceptive device without the release modifying agent.

In an aspect, the release modifying agent can increase the amount in milligrams of biologically active agent released from the contraceptive device into simulated vaginal fluid by greater than 2 over a seven-day sampling period as compared to the contraceptive device without the release modifying agent.

In an aspect, the release modifying agent can decrease the amount in milligrams of biologically active agent released from the contraceptive device into simulated vaginal fluid by greater than 1.1 over a seven-day sampling period as compared to the contraceptive device without the release modifying agent.

In an aspect, the release modifying agent can decrease the amount in milligrams of biologically active agent released from the contraceptive device into simulated vaginal fluid by greater than 1.5 over a seven-day sampling period as compared to the contraceptive device without the release modifying agent.

In an aspect, the release modifying agent can decrease the amount in milligrams of biologically active agent released from the contraceptive device into simulated vaginal fluid by greater than 2 over a seven-day sampling period as compared to the contraceptive device without the release modifying agent.

The loading of a release modifying agent is between about 1% (w/w) to about 20%. In an aspect, the loading of a preservative is between about 2% (w/w) to about 10% (w/w). In an aspect, the loading of a preservative is between about 2% (w/w) to about 6% (w/w).

One or more biologically active agents or excipients can be formulated into the ring matrix prior to forming the ring structure. These materials can be incorporated by physical mixing, using a solvent or direct incorporation into a polymer that is above its melting point. For a two-part silicone formulation, the biologically active agent or an excipient can be incorporated into one of the two parts or both of the two parts. In an aspect, at least one biologically active agent and at least one excipient is added to both part A and part B of a silastic silicone formulation. In an aspect, the silicone formulation used is Silastic Q7-4840 from Dow. In an aspect, Silastic Q7-4840 Part A and Part B comprise ferrous gluconate and ascorbic acid. In another aspect, Silastic Q7-4840 Part A and Part B comprise ferrous gluconate, ascorbic acid and compound that can modulate pH. In an aspect, the compound that can modulate pH is glycine. In another aspect, Silastic Q7-4840 Part A and Part B comprise ferrous gluconate, ascorbic acid and compound that can modulate the release of the ferrous ions. In an aspect, the compound that can modulate the release of the ferrous ions is polyglycolic acid. In another aspect, Silastic Q7-4840 Part A and Part B comprise ferrous gluconate, ascorbic acid, glycine and polyglycolic acid.

As mentioned previously, poly(ethylene-vinyl acetate) (EVA) can be used as a matrix for the ring structure of the contraceptive device. In an aspect, the EVA can have a vinyl acetate content in the 1% to 60% range. In a preferred aspect, the vinyl acetate content in about 2% to 50%. The biologically active agent or an excipient can be incorporated into the EVA through a solvent based process or through a hot-melt process or a combination thereof. For the solvent based process, the EVA can be dissolved or swollen in a suitable solvent. Suitable solvents include but are not limited to toluene, tetrahydrofuran, dichloromethane, methyl ethyl ketone (MEK) or methanol as well as combinations thereof and solutions comprising one or more of these solvents. One or more biologically active agents and one or more excipients can be added to the formulation. In one aspect, the formulation can be solvent cast into a film and the solvent evaporated to produce a material comprising the EVA, one or more biologically active agents and one or more excipients. In another aspect, the solvent can be removed without casting into a film. The composition comprising the EVA, one or more biologically active agents and one or more excipients can be milled or pelletized to produce a particulate composition. This mixture can then be hot melt extruded to form a material that comprises the biologically active agent and the excipient. Once the material has cooled, the composite mixture can be pelletized. In an aspect, the EVA, one or more biologically active agent and one or more excipient are physically mixed together. This mixture can then be hot melt extruded to form a material that comprises the biologically active agent and the excipient. Once the material has cooled, the composite mixture can be pelletized. The pelletized material can then be used to injection mold the ring portion of the contraceptive device. In an aspect, the EVA material can comprise ferrous gluconate. In another aspect, the EVA material can comprise ferrous gluconate and ascorbic acid. In another aspect, the EVA material can comprise ferrous gluconate, ascorbic acid and glycine. In another aspect, the EVA material can comprise ferrous gluconate, ascorbic acid, glycine and a polyglycolic acid.

In a contraceptive device of the present disclosure, the injection molding guide may optionally be characterized by one or more of the following exemplary features: (a) it is non-fibrous, (b) it is non-porous, (c) it is uncoated, (d) it does not contain a sizing polymer, (e) it is affixed to the porous barrier material, (f) it has a composition, and the composition is constant at each location of the injection molding guide, (g) it is biodegradable, (h) it is located along, or close to, an edge of the porous barrier material, (i) it extends into the porous barrier material, (j) it is 3D-printed onto the porous barrier material, (k) it is injected molded onto the porous barrier material, (l) it does not soften at a temperature below 120° C., while the polymeric ring may optionally be characterized by one or more of the exemplary +−+following: (a) it comprises an elastomeric polymer, (b) it comprises a biologically active agent, (c) it comprise a ferrous compound, (d) it comprises ferrous gluconate or a hydrate thereof, (e) it comprises a ferrous compound and ascorbic acid, (g) it comprises ferrous gluconate and ascorbic acid.

Manufacturing

The contraceptive device of the present disclosure may be manufactured by injection molding the ring component of the device onto the combination of the barrier material and the injection molding guide. The barrier material and the injection molding guide may be secured together so as to form a construct. The construct component of the contraceptive device is placed into a mold. The mold is closed and the ring material is injection molded onto the outer edge portion of the construct component. In an aspect, the ring component can comprise silicone that comprises one or more biologically active agents. For two-part silicone formulations as described herein, part A and part B are mixed just prior to introduction into the heated mold. The mixed silicone is injected into the heated mold and allowed to cure for a set period of time. The mold is then opened and the formed contraceptive device is removed from the mold. The rate of curing of the silicone can be controlled by increasing or decreasing the mold temperature. In an aspect, the injection molding guide is attached to the barrier material. In an aspect, the flat surfaces of the construct contact the support pins of the mold to ensure that the barrier construct remains in a suitable position to ensure that the injection molding process occurs in a reproducible manner.

In an aspect, the present disclosure provides a method of forming a contraceptive device, where the method comprises: (a) providing a construct, e.g., a construct as disclosed herein, comprising a porous barrier material affixed to an injection molding guide, the injection molding guide having symmetry and optionally comprising a plurality of planar surfaces; (b) placing the construct into a heated die; (c) adjusting a location of at least one pin within the die so that the at least one pin contacts a surface of the injection molding guide; (d) injecting a mixture of a two part heat curable polymer, e.g., a two part curable polymer as disclosed herein, into the die to form a polymeric ring, where each of the injection molding guide and the porous barrier material is at least partially embedded within the polymeric ring; (e) applying an elevated temperature, e.g., a temperature of greater than 100° C., such as 120-125° C., to the mixture of two part heat curable polymer and allowing the mixture of a two part heat curable polymer to cure in the mold such that the mixture of a two part heat curable polymer is transformed from a liquid state to a solid state; and (f) ejecting the contraceptive device from the die. Optionally, the construct is provided by a method comprising 3D-printing the injection molding guide onto the porous barrier material. Optionally, the construct is provided by a method comprising forming an injection molding guide by an injection molding process and affixing the injection molding guide to the porous barrier material In an aspect, the present disclosure provides a method of forming a contraceptive device, where the method comprises (a) providing a construct comprising a porous barrier material affixed to an injection molding guide, the injection molding guide having symmetry and optionally comprising a plurality of planar surfaces; (b) placing the construct into a die; (c) adjusting a location of at least one pin within the die so that the at least one pin contacts a planar surface of the injection molding guide; and (d) injecting a molten polymer into the die to form a polymeric ring, where each of the injection molding guide and the porous barrier material is at least partially embedded within the polymeric ring. Optionally, the construct is provided by a method comprising 3D-printing the injection molding guide onto the porous barrier material. Optionally, the construct is provided by a method comprising forming an injection molding guide by an injection molding process and affixing the injection molding guide to the porous barrier material.

In an aspect, the ring component can comprise a vaginally biocompatible thermoplastic polymer that comprises one or more biologically active agents. The thermoplastic material is introduced into the hopper of an injection molder. The material is then heated to a temperature that allows the thermoplastic material to flow under pressure. The heated thermoplastic material is then injected into the mold under pressure. The mold is cooled and then opened to release the contraceptive device. In an aspect, the thermoplastic material used is a poly(ethylene-vinyl acetate). In an aspect the thermoplastic material is a polyurethane.

In an aspect, the mold is designed such that seepage (flashing) of the injection molded material outside of the designed ring structure into the barrier material is minimized.

The contraceptive device can have a mass of about 4 g to about 8 g. In an aspect, the mass of the contraceptive device is between 4.5 g and 6.5 g. In another aspect, the mass of the contraceptive device is between 5.0 g and 6.0 g. The outer diameter of the contraceptive device can be about 45 mm to about 70 mm. In an aspect, the outer diameter can be about 45 mm to about 65 mm. In an aspect, the outer diameter can be about 52 mm to about 58 mm. In one aspect, the outer diameter of the contraceptive device has an outer diameter of about 55 mm. In another aspect, outer diameter of the contraceptive device is about 50 mm, about 51 mm, about 52 mm, about 53 mm, about 54 mm, about 56 mm, about 57 mm, about 58 mm, about 59 mm or about 60 mm.

Optionally, the two-dimensional surface area of the elastomeric ring component is about 40% to about 55% of the two dimensional surface area of the contraceptive device. Optionally, the two-dimensional surface area of the exposed barrier component is about 45% to about 60% of the two dimensional surface area of the contraceptive device.

In one aspect the contraceptive device comprises a ring component, a porous barrier material and an injection molding guide, each of the injection molding guide and the porous barrier material at least partially embedded within the ring component, where the injection molding guide comprises a plurality of planar surfaces and the ring component is formed from polymer and may be identified as a polymeric ring. In one aspect the contraceptive device comprises a ring component, a porous barrier material, an injection molding guide, and one or more biologically active agents, each of the injection molding guide and the porous barrier material at least partially embedded within the ring component, where the injection molding guide comprises a plurality of planar surfaces and the ring component is formed from polymer and may be identified as a polymeric ring. In one aspect, the contraceptive device comprises a ring component, a barrier component, and one or more biologically active agent. In another aspect, the contraceptive device comprises a ring component, a barrier component, one or more biologically active agent and one or more excipient. In another aspect, the contraceptive device comprises a ring component, a barrier component that has an injection molding guide attached to it, and one or more biologically active agent. In another aspect, the contraceptive device comprises a ring component, a barrier component that has an injection molding guide attached to it, one or more biologically active agent and one or more excipient. In an aspect, the injection molding guide portion that is attached to the barrier material is embedded within the ring component. In another aspect, the contraceptive device comprises a ring component, and a barrier component. In another aspect, the contraceptive device comprises a ring component, a barrier component, and one or more excipients.

In an aspect, the contraceptive device comprises a silicone ring component, an absorbable mesh barrier component, ferrous gluconate dihydrate and ascorbic acid. In an aspect, the absorbable mesh comprises lactide and trimethylene carbonate residues. In an aspect, the contraceptive device comprises a silicone ring component, an absorbable mesh barrier component comprising lactide and trimethylene carbonate residues, ferrous gluconate dihydrate, ascorbic acid, glycine and polyglycolic acid particles.

In an aspect, the contraceptive device comprises a polymeric ring, a porous barrier material and an injection molding guide, each of the injection molding guide and the porous barrier material at least partially embedded within the polymeric ring, where optionally the injection molding guide is affixed to the porous barrier material. In an aspect, the contraceptive device comprises a polymeric ring, a porous barrier material and an injection molding guide, the injection molding guide entirely embedded within the polymeric ring and the porous barrier material partially embedded within the polymeric ring, where optionally the injection molding guide is affixed to the porous barrier material. While the contraceptive device may be prepared from a construct wherein the injection molding guide is affixed to the porous barrier material, it may occur that at some time after preparation of the contraceptive device, for example during packaging, the injection molding guide becomes un-affixed to the porous barrier material, although the injection molding guide remains at least partially embedded, and optionally entirely embedded, within the polymeric ring. Thus, the present disclosure provides a contraceptive device comprising a polymeric ring, a porous barrier material and an injection molding guide, each of the injection molding guide and the porous barrier material at least partially embedded within the polymeric ring, where optionally the injection molding guide is affixed to the porous barrier material. In these aspects, the injection molding guide may be characterized as having symmetry and may optionally comprise a plurality of planar surfaces, whether or not the injection molding guide is affixed to the porous barrier material. For example, in an aspect, the contraceptive device comprises a polymeric ring, a porous barrier material and an injection molding guide, each of the injection molding guide and the porous barrier material at least partially embedded within the polymeric ring, where the injection molding guide is affixed to the porous barrier material, and where the injection molding guide is symmetrical and optionally comprises a plurality of planar surfaces. As another example, in an aspect, the contraceptive device comprises a polymeric ring, a porous barrier material and an injection molding guide, the injection molding guide entirely embedded within the polymeric ring and the porous barrier material partially embedded within the polymeric ring, where the injection molding guide is affixed to the porous barrier material, and where the injection molding guide is symmetrical and optionally comprises a plurality of planar surfaces. As another example, in an aspect, the contraceptive device comprises a polymeric ring, a porous barrier material and an injection molding guide, each of the injection molding guide and the porous barrier material at least partially embedded within the polymeric ring, where the injection molding guide is not affixed to the porous barrier material, and where the injection molding guide is symmetrical and comprises a plurality of planar surfaces. As another example, in an aspect, the contraceptive device comprises a polymeric ring, a porous barrier material and an injection molding guide, the injection molding guide entirely embedded within the polymeric ring and the porous barrier material partially embedded within the polymeric ring, where the injection molding guide is not affixed to the porous barrier material, and where the injection molding guide is symmetrical and optionally comprises a plurality of planar surfaces.

In one aspect, the disclosure provides a contraceptive device comprising a polymeric ring, a porous barrier material and an injection molding guide, the injection molding guide being symmetrical and comprising a plurality of planar surfaces, wherein the injection molding guide is completely embedded within the polymeric ring and the porous barrier material is partially embedded within the polymeric ring, wherein at least two of the plurality of planar surfaces intersect with one another to form a corner.

In one aspect, the present disclosure provides a contraceptive device comprising a polymeric ring, a porous barrier material and an injection molding guide, the injection molding guide being symmetrical and comprising a plurality of planar surfaces, wherein the injection molding guide is completely embedded within the polymeric ring and the porous barrier material is partially embedded within the polymeric ring, wherein the injection molding guide comprises a plurality of corners, each of the plurality of corners formed by intersection of two of the plurality of planar surfaces.

In one aspect, the present disclosure provides a contraceptive device comprising a polymeric ring, a porous barrier material and an injection molding guide, the injection molding guide being symmetrical and comprising a plurality of planar surfaces, wherein the injection molding guide is completely embedded within the polymeric ring and the porous barrier material is partially embedded within the polymeric ring, wherein the injection molding guide comprises a plurality of corners, each of the plurality of corners formed by intersection of two of the plurality of planar surfaces, and wherein a cross-section of the injection molding guide comprises two shapes selected from an L-shape and a T-shape.

In one aspect, the present disclosure provides a contraceptive device comprising a polymeric ring, a porous barrier material and an injection molding guide, the injection molding guide being a symmetrical annular ring comprising a plurality of planar surfaces, wherein the injection molding guide is completely embedded within the polymeric ring and the porous barrier material is partially embedded within the polymeric ring, wherein at least two of the plurality of planar surfaces intersect with one another to form a corner.

In one aspect, the present disclosure provides a contraceptive device comprising a polymeric ring, a porous barrier material and an injection molding guide, the injection molding guide being symmetrical and comprising a plurality of planar surfaces, wherein the injection molding guide is completely embedded within the polymeric ring and the porous barrier material is partially embedded within the polymeric ring, wherein the injection molding guide comprises a plurality of corners, each of the plurality of corners formed by intersection of two of the plurality of planar surfaces, and wherein a cross-section of the injection molding guide comprises two shapes that are complementary to one another.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical. The injection molding guide may be characterized by one or more of the following: (a) it is non-fibrous, (b) it is non-porous, (c) it is uncoated, (d) it does not contain a sizing polymer, (e) it is affixed to the porous barrier material, (f) it has a composition, and the composition is constant at each location of the injection molding guide, (g) it is biodegradable, (h) it is located along, or close to, an edge of the porous barrier material, (i) it extends into the porous barrier material, (j) it is 3D-printed onto the porous barrier material, (k) it is injected molded onto the porous barrier material, (l) it does not soften at a temperature below 120° C.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical. The polymeric ring may be characterized by one or more of the following: (a) it comprises an elastomeric polymer, (b) it comprises a biologically active agent, (c) it comprise a ferrous compound, (d) it comprises ferrous gluconate or a hydrate thereof, (e) it comprises a ferrous compound and ascorbic acid, (g) it comprises ferrous gluconate and ascorbic acid.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical and comprises a planar surface. The injection molding guide may be characterized by one or more of the following: (a) it is non-fibrous, (b) it is non-porous, (c) it is uncoated, (d) it does not contain a sizing polymer, (e) it is affixed to the porous barrier material, (f) it has a composition, and the composition is constant at each location of the injection molding guide, (g) it is biodegradable, (h) it is located along, or close to, an edge of the porous barrier material, (i) it extends into the porous barrier material, (j) it is 3D-printed onto the porous barrier material, (k) it is injected molded onto the porous barrier material, (l) it does not soften at a temperature below 120° C.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical and comprises a planar surface. The polymeric ring may be characterized by one or more of the following: (a) it comprises an elastomeric polymer, (b) it comprises a biologically active agent, (c) it comprise a ferrous compound, (d) it comprises ferrous gluconate or a hydrate thereof, (e) it comprises a ferrous compound and ascorbic acid, (g) it comprises ferrous gluconate and ascorbic acid.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical and comprises a plurality of planar surfaces. The injection molding guide may be characterized by one or more of the following: (a) it is non-fibrous, (b) it is non-porous, (c) it is uncoated, (d) it does not contain a sizing polymer, (e) it is affixed to the porous barrier material, (f) it has a composition, and the composition is constant at each location of the injection molding guide, (g) it is biodegradable, (h) it is located along, or close to, an edge of the porous barrier material, (i) it extends into the porous barrier material, (j) it is 3D-printed onto the porous barrier material, (k) it is injected molded onto the porous barrier material, (l) it does not soften at a temperature below 120° C.

In one aspect, the present disclosure provides a contraceptive device comprising a polymeric ring, a porous barrier material and an injection molding guide, wherein the injection molding guide is completely embedded within the polymeric ring and the porous barrier material is partially embedded within the polymeric ring, where the polymeric ring encircles the porous barrier material, where the barrier material is a mesh, and where the injection molding guide is symmetrical and comprises a plurality of planar surfaces. The polymeric ring may be characterized by one or more of the following: (a) it comprises an elastomeric polymer, (b) it comprises a biologically active agent, (c) it comprise a ferrous compound, (d) it comprises ferrous gluconate or a hydrate thereof, (e) it comprises a ferrous compound and ascorbic acid, (g) it comprises ferrous gluconate and ascorbic acid.

Packaging

The contraceptive device can be placed in a protective packaging. The protective packaging can protect the contraceptive device from mechanical damage, light, moisture absorption, pathogens, dust, particulates or a combination thereof. The protective packaging can be called the primary packaging. The packaging material used can comprise high density polyethylene, polyethylene terephthalate (PET), polyethylene terephthalate glycol (PETG), polyvinyl chloride (PVC), polycarbonate (PC), polypropylene (PP), high impact polystyrene (HIPS), Ovantex®, foil or a combination thereof. High density polyethylene packaging can be in the form of a Tyvek® pouch. In an aspect the contraceptive device can be packaged in a Tyvek® Pouch that is heat sealed. In an aspect, the contraceptive device can be packaged in a foil pouch that is heat sealed. In an aspect, the foil pouch can comprise an aluminum foil. In an aspect, the contraceptive device can be packaged with a moisture absorbent material, an oxygen absorbent material or both a moisture absorbent material and an oxygen absorbent material. In an aspect, the environment within the packaging of the packaged device can comprise less than 10% oxygen. In an aspect, the environment within the packaging of the packaged device can comprise less than 5% oxygen. In an aspect, the environment within the packaging of the packaged device can comprise less than 1% oxygen. In an aspect, the environment within the packaging of the packaged device can comprise less than 20% humidity. In an aspect, the environment within the packaging of the packaged device can comprise less than 10% humidity. In an aspect, the environment within the packaging of the packaged device can comprise less than 1% humidity.

In an aspect, a packaged contraceptive product can comprise a desiccant, an oxygen scavenger or both a desiccant and an oxygen scavenger. The desiccant or oxygen scavenger can be packaged in the primary packaging together with the contraceptive device. The desiccant or oxygen scavenger can be packaged in a foil pouch that contains the contraceptive device within its primary packaging.

In an aspect, the protective packaging that contains the device is sealed using a heat sealing process. In an aspect, the protective packaging can comprise a reclosable foil pouch. In an aspect the resealable foil pouch can comprise aluminum foil.

The contraceptive device can be packaged in a secondary packaging material. The secondary packaging can contain the contraceptive device that is packaged in a primary packaging. The secondary packaging can comprise a cellulose based material. The secondary packaging can comprise cardboard. The secondary packaging can comprise a carton. In an aspect, the carton can comprise a chipboard carton.

The packaged contraceptive device can comprise a contraceptive device of the invention, a primary packing component, and a secondary packaging component. In an aspect, the packaged contraceptive device and further comprise a set of instructions for use.

In an aspect, the packaged contraceptive device can comprise a contraceptive device that comprises, a silicone ring, a barrier material, ferrous gluconate within the silicone ring, ascorbic acid within the silicone ring, a foil primary packaging, a secondary packaging carton and a set of instructions for use or prescribing information.

The contraceptive device can be sterile. The contraceptive device can be sterilized using an alcohol solution, by exposing the device to ethylene oxide, ionizing radiation, autoclaving, ultra-violet radiation or dry heat. Alcohol solutions that can be used include but are not limited to methanol, ethanol, isopropanol and aqueous solutions thereof. The ionizing radiation used can include gamma radiation and electron beam radiation. The dose of ionizing radiation used for sterilization is greater than 20 kGy, greater than 25 kGy, greater than 30 kGy, greater than 35 kGy or greater than 40 kGy. In a preferred aspect, the radiation is greater than 25 kGy. For a contraceptive device that is sterilized using ethylene oxide, the final contraceptive product complies with ISO 10993-7 for residual ethylene oxide and ethylene chlorohydrin levels. In an aspect, residual ethylene oxide levels are such that the average daily dose of ethylene oxide to the patient is less than 2 mg/day. In an aspect, residual ethylene oxide levels are such that the average daily dose of ethylene oxide to the patient is less than 0.1 mg/day. In another aspect, residual ethylene oxide levels are such that the maximum ethylene oxide dose to the patient is less than 4 mg in the first 24 hours. In another aspect, residual ethylene oxide levels are such that the maximum ethylene oxide dose to the patient is less than 60 mg in the first 30 days. In an aspect, residual ethylene chlorohydrin levels are such that the average daily dose of ethylene chlorohydrin to the patient is less than 2 mg/day. In an aspect, residual ethylene chlorohydrin levels are such that the average daily dose of ethylene chlorohydrin to the patient is less than 0.4 mg/day. In another aspect, residual ethylene chlorohydrin levels are such that the maximum ethylene chlorohydrin dose to the patient is less than 9 mg in the first 24 hours. In another aspect, residual ethylene chlorohydrin levels are such that the maximum ethylene chlorohydrin dose to the patient is less than 60 mg in the first 30 days.

The contraceptive device can be in a non-sterile form. In an aspect, the non-sterile contraceptive device complies to USP <1111>. The non-sterile contraceptive device can have a total aerobic microbial count (cfu/g or cfu/mL) of $10^2$ or less. The non-sterile contraceptive device can have a total combined yeasts/molds count (cfu/g or cfu/mL) of $10^1$ or less. The non-sterile contraceptive device can have a total aerobic microbial count (cfu/g or cfu/mL) of $10^2$ or less and a total combined yeasts/molds count (cfu/g or cfu/mL) of $10^1$ or less. The non-sterile contraceptive device cannot be contaminated with *Pseudomonas aeruginosa, Staphylococcus aureus* or *Candida albicans*.

The contraceptive device can be contaminated with bacterial endotoxin. In an aspect, the contaminated contraceptive device should have a bacterial endotoxin contamination level of less than or equal to 20 EU per device.

The ring can be inserted into an applicator to facilitate deployment of the contraceptive device into the vagina. The applicator can comprise a polymer. Suitable polymers for the applicator are polypropylene, polyethylene, high density polyethylene, low density polyethylene, medium density polyethylene, polyurethane, polystyrene, nylon, polyvinyl chloride or a blend thereof. The applicator can comprise two or more different polymers. In an aspect, the applicator is made from polypropylene. In an aspect, the applicator can comprise a lubricant material that reduces the friction between the components of the applicator. Suitable lubricants include but are not limited to demethicone, liquid polydimethylsiloxane, fatty acid amides, polyethylene glycol, glycerine, silicone oil, propylene glycol or a combination thereof. In an aspect, the applicator further comprises a dye. The dye can impart a green, blue, violet, pink, orange, yellow, red, purple or white color.

The applicator described in WO2016156403 can be used for the contraceptive device of this invention and is incorporated by reference herein.

Prior to use, the contraceptive device must be removed from the primary packaging. The contraceptive device can be inserted into the vagina. The contraceptive device can be inserted with the user lying down, squatting, or standing with one leg raised up. The contraceptive device is placed in the vagina in such a manner that is acts as a physical barrier between the lower part of the vagina and the cervical os. The contraceptive device can be inserted into the vagina on day 1 of the menstrual cycle. The contraceptive device can be inserted into the vagina on day 2 through day 5 of the menstrual cycle. The contraceptive device can be inserted into the vagina using one or more fingers. The contraceptive device can be inserted into the vagina using an applicator. In an aspect, the contraceptive device is biocompatible as assessed through ISO10993 testing. In an aspect, use of the contraceptive device does not significantly change the genital flora as assessed using semi-quantitative cultures from the vagina.

In an aspect, once the contraceptive device is placed in the vagina, the vaginal pH remains below pH 4.6 except up to 6 hours post-coitus. The contraceptive device releases ferrous ions and/or ferrous salt into the vagina. The ferrous gluconate measured in the vaginal fluid prior to coitus is greater than 100 ug/g vaginal fluid. In an aspect, the ferrous gluconate measured in the vaginal fluid prior to coitus is greater than 500 ug/g vaginal fluid. In another aspect, the ferrous gluconate measured in the vaginal fluid prior to coitus is greater than 1000 ug/g vaginal fluid.

When placed in simulated vaginal fluid, the contraceptive device will release at least 5 mg of ferrous gluconate per 7 days for at least 35 days. In an aspect, when placed in simulated vaginal fluid, the contraceptive device will release at least 10 mg of ferrous gluconate per 7 days for at least 35 days. When placed in simulated vaginal fluid, the contraceptive device will release at least 2 mg of ascorbic acid per 7 days for at least 35 days. In an aspect, when placed in simulated vaginal fluid, the contraceptive device will release at least 5 mg of ascorbic acid per 7 days for at least 35 days.

Kit

The present disclosure comprises a kit comprising a contraceptive medical device as disclosed herein, contained within a container. The kit optionally further comprises one or more of a lubricant, a spermicidal gel or film, a contraceptive gel and/or an applicator. The kit may further comprise written instructions for its use.

EXEMPLARY EMBODIMENTS

The present disclosure provides the following numbered embodiments, which are only exemplary and not exhaustive of the embodiments provided in the various aspects and embodiments disclosed herein.

1) A contraceptive device comprising a porous barrier material and an injection molding guide, the injection molding guide comprising a plurality of planar surfaces, the injection molding guide encased within a polymeric ring structure, where optionally the injection molding guide and the porous barrier material are affixed to one another.

2) The contraceptive device of embodiment 1 wherein the barrier material is a mesh.

3) The contraceptive device of embodiments 1-2 wherein the barrier material is fibrous.

4) The contraceptive device of embodiments 1-3 wherein the barrier material is circular.

5) The contraceptive device of embodiments 1-3 wherein the barrier material is substantially circular.

6) The contraceptive device of embodiments 1-5 wherein the barrier material has a diameter of about 45 mm to about 53 mm.

7) The contraceptive device of embodiments 1-6 wherein the injection molding guide is non-fibrous.

8) The contraceptive device of embodiments 1-7 where the injection molding guide has three (3) planar surfaces.

9) The contraceptive device of embodiments 1-7 where the injection molding guide has six (6) planar surfaces.

10) The contraceptive device of embodiments 1-7 where the injection molding guide has eight (8) planar surfaces.

11) The contraceptive device of embodiments 1-10 wherein the injection molding guide has a melting point above 120° C.

12) The contraceptive device of embodiments 1-11 wherein the injection molding guide has a uniform cross-section at all locations around the injection molding guide.

13) The contraceptive device of embodiments 1-12 wherein the injection molding guide has a corner formed by two planar surfaces intersecting at an angle of 85 to 95 degrees.

14) The contraceptive device of embodiments 1-13 wherein the injection molding guide is uncoated.

15) The contraceptive device of embodiments 1-14 wherein the injection molding guide does not contain a sizing polymer.

16) The contraceptive device of embodiments 1-15 wherein the injection molding guide has a single composition throughout the support ring.

17) The contraceptive device of embodiments 1-16 wherein the injection molding guide is biodegradable.

18) The contraceptive device of embodiments 1-16 wherein the injection molding guide is non-biodegradable.

19) The contraceptive device of embodiments 1-18 wherein the injection molding guide is located along an edge of the barrier material.

20) The contraceptive device of embodiments 1-18 wherein the injection molding guide is located close to an edge of the barrier material.

21) The contraceptive device of embodiments 1-20 wherein the injection molding guide extends into the porous barrier material.

22) The contraceptive device of embodiments 1-21 wherein the injection molding guide is 3D-printed on the barrier material.

23) The contraceptive device of embodiments 1-21 wherein the injection molding guide is injected molded onto the barrier material.

24) The contraceptive device of embodiments 1-23 wherein the ring structure comprises an elastomeric polymer.

25) The contraceptive device of embodiments 1-24 wherein the ring structure comprises silicone.

26) The contraceptive device of embodiments 1-24 wherein the ring structure comprises poly(ethylene-vinyl acetate).

27) The contraceptive device of embodiments 1-26 further comprising a biologically active agent located within the polymeric ring structure.

28) The contraceptive device of embodiments 1-27 further comprising a ferrous compound located within the polymeric ring structure.

29) The contraceptive device of embodiments 1-27 further comprising ferrous gluconate or a hydrate thereof located within the polymeric ring structure.

30) The contraceptive device of embodiments 1-27 further comprising a ferrous compound and ascorbic acid, each located within the polymeric ring structure.

31) The contraceptive device of embodiments 1-27 further comprising ferrous gluconate or a hydrate thereof and ascorbic acid, each located within the polymeric ring structure.

32) A kit comprising the contraceptive device of any of embodiments 1-31, the kit further comprising at least one of a lubricant, a spermicidal gel, a spermicidal film, a contraceptive gel and an applicator.

33) The kit of embodiment 32 further comprising a polymeric applicator.

34) The kit of embodiments 32-33 further comprising a set of instructions for use.

35) A construct for forming a contraceptive device, the construct comprising a porous barrier material affixed to an injection molding guide, the injection molding guide comprising a plurality of planar surfaces.

36) The construct of embodiment 35 wherein the barrier material is a mesh.

37) The construct of embodiments 35-36 wherein the barrier material is fibrous.

38) The construct of embodiments 35-37 wherein the barrier material is circular.

39) The construct of embodiments 35-37 wherein the barrier material is substantially circular.

40) The construct of embodiments 35-39 wherein the barrier material has a diameter or maximum distance between two furthest edges of about 45 mm to about 53 mm.

41) The construct of embodiments 35-40 wherein the injection molding guide is non-fibrous.

42) The construct of embodiments 35-41 wherein the injection molding guide has a melting point above 120° C.

43) The construct of embodiments 35-42 wherein the injection molding guide has a uniform cross-section at all locations around the injection molding guide.

44) The construct of embodiments 35-43 wherein the injection molding guide has a corner formed by two planar surfaces intersecting at an angle of 85 to 95 degrees.

45) The construct of embodiments 35-44 wherein the injection molding guide is uncoated.

46) The construct of embodiments 35-45 wherein the injection molding guide does not contain a sizing polymer.

47) The construct of embodiments 35-46 wherein the injection molding guide has a single composition throughout the support ring.

48) The construct of embodiments 35-47 wherein the injection molding guide is biodegradable.

49) The construct of embodiments 35-48 wherein the injection molding guide is located along an edge of the barrier material.

50) The construct of embodiments 35-48 wherein the injection molding guide is located close to an edge of the barrier material.

51) The construct of embodiments 35-50 wherein the injection molding guide extends into the porous barrier material.

52) The construct of embodiments 35-51 wherein the injection molding guide is 3D-printed on the barrier material.

53) The construct of embodiments 35-52 wherein the injection molding guide is injected molded onto the barrier material.

54) A method of forming a contraceptive device, the method comprising:

a. providing a construct comprising a porous barrier material affixed to an injection molding guide, the injection molding guide comprising a plurality of planar surfaces;

b. placing the construct into a die;

c. adjusting a location of at least one pin within the die so that the at least one pin contacts a surface of the injection molding guide; and d. injecting a molten polymer into the die to form a ring structure that encases the injection molding guide.

55) The method of embodiment 54 wherein the construct is provided by a method comprising 3D-printing the injection molding guide onto the porous barrier material.

56) The method of embodiment 54 wherein the construct is provided by a method comprising:

a. forming an injection molding guide by an injection molding process;

b. affixing the injection molding guide to the porous barrier material.

57) The method of embodiments 54-56 wherein the contraceptive device is a contraceptive device according to any of embodiments 1-31.

58) The method of embodiments 54-56 wherein the construct is a construct according to any of embodiments 35-53.

Thus, the present disclosure provides, for example:

1) A contraceptive device comprising a porous barrier material affixed to an injection molding guide, the injection molding guide comprising a plurality of planar surfaces, the injection molding guide encased within a polymeric ring structure.

2) The contraceptive device of embodiment 1 wherein the barrier material is a mesh.

3) The contraceptive device of embodiment 1 wherein the barrier material is fibrous.

4) The contraceptive device of embodiment 1 wherein the barrier material is circular.

5) The contraceptive device of embodiment 1 wherein the barrier material is substantially circular.

6) The contraceptive device of embodiment 1 wherein the barrier material has a diameter of about 45 mm to about 53 mm 7) The contraceptive device of embodiment 1 wherein the injection molding guide is non-fibrous.

8) The contraceptive device of embodiment 1 wherein the injection molding guide has a softening point above 120° C.

9) The contraceptive device of embodiment 1 wherein the injection molding guide has a uniform cross-section at all locations around the injection molding guide.

10) The contraceptive device of embodiment 1 wherein the injection molding guide has a corner formed by two planar surfaces intersecting at a 90 degree angle.

11) The contraceptive device of embodiment 1 wherein the injection molding guide is uncoated.

12) The contraceptive device of embodiment 1 wherein the injection molding guide does not contain a sizing polymer.

13) The contraceptive device of embodiment 1 wherein the injection molding guide has a single composition throughout the support ring.

14) The contraceptive device of embodiment 1 wherein the injection molding guide is biodegradable.

15) The contraceptive device of embodiment 1 wherein the injection molding guide is located along an edge of the barrier material.

16) The contraceptive device of embodiment 1 wherein the injection molding guide is located close to an edge of the barrier material.

17) The contraceptive device of embodiment 1 wherein the injection molding guide extends into the porous barrier material.

18) The contraceptive device of embodiment 1 wherein the injection molding guide is 3D-printed on the barrier material.

19) The contraceptive device of embodiment 1 wherein the injection molding guide is injected molded onto the barrier material.

20) The contraceptive device of embodiment 1 wherein the ring structure comprises an elastomeric polymer.

21) The contraceptive device of embodiment 1 further comprising a biologically active agent located within the polymeric ring structure.

22) The contraceptive device of embodiment 1 further comprising a ferrous compound located within the polymeric ring structure.

23) The contraceptive device of embodiment 1 further comprising ferrous gluconate or a hydrate thereof located within the polymeric ring structure.

24) The contraceptive device of embodiment 1 further comprising a ferrous compound and ascorbic acid, each located within the polymeric ring structure.

25) A kit comprising the contraceptive device of embodiment 1, the kit further comprising at least one of a lubricant, a spermicidal gel, a spermicidal film, a contraceptive gel and an applicator.

26) A construct for forming a contraceptive device, the construct comprising a porous barrier material affixed to an injection molding guide, the injection molding guide comprising a plurality of planar surfaces.

27) The construct of embodiment 26 wherein the barrier material is a mesh.

28) The construct of embodiment 26 wherein the barrier material is fibrous.

29) The construct of embodiment 26 wherein the barrier material is circular.

30) The construct of embodiment 26 wherein the barrier material is substantially circular.

31) The construct of embodiment 26 wherein the barrier material has a diameter of about 45 mm to about 53 mm 32) The construct of embodiment 26 wherein the injection molding guide is non-fibrous.

33) The construct of embodiment 26 wherein the injection molding guide has a softening point above 120° C.

34) The construct of embodiment 26 wherein the injection molding guide has a uniform cross-section at all locations around the injection molding guide.

35) The construct of embodiment 26 wherein the injection molding guide has a corner formed by two planar surfaces intersecting at a 90 degree angle.

36) The construct of embodiment 26 wherein the injection molding guide is uncoated.

37) The construct of embodiment 26 wherein the injection molding guide does not contain a sizing polymer.

38) The construct of embodiment 26 wherein the injection molding guide has a single composition throughout the support ring.

39) The construct of embodiment 26 wherein the injection molding guide is biodegradable.

40) The construct of embodiment 26 wherein the injection molding guide is located along an edge of the barrier material.

41) The construct of embodiment 26 wherein the injection molding guide is located close to an edge of the barrier material.

42) The construct of embodiment 26 wherein the injection molding guide extends into the porous barrier material.

43) The construct of embodiment 26 wherein the injection molding guide is 3D-printed on the barrier material.

44) The construct of embodiment 26 wherein the injection molding guide is injected molded onto the barrier material.

45) A method of forming a contraceptive device, the method comprising:
   a. providing a construct comprising a porous barrier material affixed to an injection molding guide, the injection molding guide comprising a plurality of planar surfaces;
   b. placing the construct into a die;
   c. adjusting a location of at least one pin within the die so that the at least one pin contacts a surface of the injection molding guide; and
   d. injecting a molten polymer into the die to form a ring structure that encases the injection molding guide.
46) The method of embodiment 45 wherein the construct is provided by a method comprising 3D-printing the injection molding guide onto the porous barrier material.
47) The method of embodiment 45 wherein the construct is provided by a method comprising:
   a. forming an injection molding guide by an injection molding process;
   b. affixing the injection molding guide to the porous barrier material.
48) The method of embodiment 45 wherein the molten polymer is a mixture of a two part heat curable polymer.

As also mentioned elsewhere herein, the present disclosure provides that aspects and embodiments as disclosed herein may be combined in order to describe a contraceptive medical device, and construct, or a related method, of the present disclosure. For example, the present disclosure provides a contraceptive device comprising a porous barrier material and an injection molding guide, the injection molding guide comprising a plurality of planar surfaces, the injection molding guide encased within a polymeric ring structure which is elastomeric and which contains a biologically active agent, where the injection molding guide and the porous barrier material are affixed to one another and where the barrier material is a circular mesh having a diameter of about 45 mm to about 53 mm, and where the injection molding guide has a uniform cross-sectional shape (profile) at all locations with the cross section having at least three (3) planar surfaces, the injection molding guide also having a melting point above the temperature used for injection molding. The injection molding guide may be prepared by 3D-printing or injection molding, as two options, and may be further characterized as being non-fibrous, uncoated (e.g., no sizing polymer located on the injection molding guide), and formed from a single composition rather than being a hybrid of two or more different compositions. The injection molding guide may be located flush along the outside edge, i.e., the perimeter, of the circular or substantially circular barrier material, although optionally it may be located close to the outer edge of the barrier material. When the injection molding guide is 3D-printed onto the barrier material, the molten material used to make the injection molding guide may sink into the porous barrier material, and thus the injection molding guide may partially extend into the porous barrier material. In this way, the injection molding guide may become affixed to the porous barrier material. When the injection molding guide is injection molded separate from the porous barrier material, the injection molding guide may be affixed through an adhesive or the like to the barrier material.

Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, EIZ specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. % or % w/w) of a component, unless specifically stated to the contrary, is based on the total weight of the formulation or composition in which the component is included.

As used herein, when a compound is referred to as a monomer or a compound, it is understood that this is not interpreted as one molecule or one compound. For example, two monomers generally refers to two different monomers, and not two molecules.

As used herein, the terms "optional" or "optionally" means that the subsequently described event or circumstance can or cannot occur, and that the description includes instances where said event or circumstance occurs and instances where it does not.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, a mammalian subject is a human. A patient refers to a subject afflicted with a disease or disorder or requiring contraception. The term "patient" includes human and veterinary subjects.

As used herein, the terms "administering" and "administration" refer to any method of providing a disclosed contraceptive composition to a subject.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The transitional phrase "consisting of" excludes any element, step, or ingredient not specified in the claim, closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" limits the scope of a claim to the specified materials or steps and those that do not materially affect the basic and novel characteristic(s) of the claimed invention. A 'consisting essentially of' claim occupies a middle ground between closed claims that are written in a 'consisting of' format and fully open claims that are drafted in a 'comprising' format. Optional additives as defined herein, at a level that is appropriate for such additives, and minor impurities are not excluded from a composition by the term "consisting essentially of".

When a composition, a process, a structure, or a portion of a composition, a process, or a structure, is described herein using an open-ended term such as "comprising," unless otherwise stated the description also includes an embodiment that "consists essentially of" or "consists of" the elements of the composition, the process, the structure, or the portion of the composition, the process, or the structure.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

The term "or", as used herein, is inclusive; that is, the phrase "A or B" means "A, B, or both A and B. More specifically, a condition "A or B" is satisfied by any one of" the following: A is true (or present) and B is false (or not present); A is false (or not present) and B is true (or present); or both A and B are true (or present). Exclusive "or" is designated herein by terms such as "either A or B" and "one of A or B", for example.

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

When materials, methods, or machinery are described herein with the term "known to those of skill in the art", "conventional" or a synonymous word or phrase, the term signifies that materials, methods, and machinery that are conventional at the time of filing the present application are encompassed by this description. Also encompassed are materials, methods, and machinery that are not presently conventional, but that will have become recognized in the art as suitable for a similar purpose.

Unless stated otherwise, all percentages, parts, ratios, and like amounts, are defined by weight.

All patents, patent applications and references included herein are specifically incorporated by reference in their entireties.

It should be understood, of course, that the foregoing relates only to preferred embodiments of the present disclosure and that numerous modifications or alterations may be made therein without departing from the spirit and the scope of the disclosure as set forth in this disclosure.

The present disclosure is further illustrated by the examples contained herein, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

EXAMPLES

Example 1

Synthesis of Lactoprene® 8812 Polymer

A polyaxial polymer comprising lactide and trimethylene carbonate was synthesized according to U.S. Pat. No. 7,048,753. The lactide to trimethylene carbonate ratio used in the synthesis was 88:12. The polymer was then ground to smaller particle size.

Example 2

Extrusion into Multifilament Yarn—43

Lactoprene® 8812 polymer was placed in a Novatec polymer dryer and dried at 110° C. for about 1 hr. 45 min. The polymer was then extruded through a 43 hole die with each hole having an inside diameter of 12 mils to provide an extruded multifilament yarn. A spin finish (Lurol® PT-6A spin finish) was applied to the extruded yarn. The extruded yarn was then oriented on a set of godets. The yarn was then reoriented on a set of Godets until the yarn had a denier (g/9000 m) of between 80 and 100 and an elongation of 20-40%.

Example 3

Extrusion into Multifilament Yarn—86

Lactoprene® 8812 polymer was placed in a Novatec polymer dryer and dried at 110° C. for about 1 hr 45 min. The polymer was then extruded through an 86 hole die with each hole having an inside diameter of 25 mils to provide an extruded multifilament yarn. A spin finish (Lurol® PT-6A spin finish) was applied to the extruded yarn. The extruded yarn was then oriented on a set of godets. The yarn was then reoriented on a set of Godets until the yarn had a denier (g/9000 m) of between 80 and 100 and an elongation of 20-40%.

Example 4

Extrusion into a Monofilament Yarn

Lactoprene® 8812 polymer was extruded into a mono-filament that has a final diameter of about 1.75 mm.

Example 5

Knitted Mesh

The lactide-co-TMC polymer multifilament yarn (Example 2) was wound and warped into a 2 ply yarn using a SSM winder and a LIBA GE203A, high speed warping machine. The 2-ply yarn was knitted into a mesh using a LIBA Racop 4-O, 9 gauge, 4-bar knitting machine. Guide bars 2 and 3 were used for knitting. The knitter was setup for thirty eight courses per inch and 2 bar tricot pattern.

Example 6

Knitted Mesh Cleaning

The mesh (Example 5) was cut into lengths of about 68 cm to provide mesh panels. The mesh panels were placed in a glass jar. The jar was then filled to within about 1 inch from the top of the jar with isopropyl alcohol (IPA). The jar was sealed and was then placed on a jar roller mill for 10-20 minutes at the highest speed setting. The mesh panels were removed from the jar. The washing process was repeated with fresh IPA. After washing, the mesh panels were allowed to air dry for at least 60 minutes. The mesh panels were then dried under full vacuum for 2 hrs.

Example 7

Residual Spin Finish

The residual spin finish (Lurol® PT-6A spin finish) in the mesh of the construct of Example 10 was analyzed using HPLC analysis. An approximately 800 mg sample of a Lactoprene 8812 mesh from the construct from Example 10 was placed in a 40 mL glass scintillation vial. About 8 mL of an isopropanol solution that contained about 2.5% (v/v) cyclohexane was added to the sample. The sample was placed on an orbital shaker for 4 hrs. The sample was then allowed to stand until the majority of the fibers had settled.

An aliquot of the solution from the sample was diluted 1:1 with water. The diluted aliquot was analyzed by HPLC using a C8 column, a water/acetonitrile gradient and an ELSD detector, and the diluted aliquot was analyzed twice, i.e., two runs were performed on each sample. A standard curve using Lurol® PT-6A spin finish was prepared. This process was repeated twice, so that a total of three constructs were analyzed in six runs. The residual levels of spin finish are shown in Table 1.

TABLE 1

| Residual spin finish in mesh | |
|---|---|
| Sample Set Description | Maximum Residual Spin Finish (% w/w) |
| Range for 6 runs (3 constructs, 2 runs/construct) | 0.045 to 0.065 |
| Range of averages per construct (2 runs/construct) | 0.045 to 0.064 |
| Range of standard deviations per construct (2 runs/construct) | 0.000 to 0.001 |

Example 8

Heat Setting of the Knitted Mesh

A washed mesh panel of Example 6 was placed in a pin frame and tension was applied to the mesh within the frame. The pin frame with the mesh panel was placed in an oven set at about 145° C. for about 3 minutes. Once cooled, the mesh panel was removed from the pin frame. This process was repeated with several different mesh panels. The heat set mesh panels had the following properties, see Table 2, where I.V. refers to the intrinsic viscosity of the dissolved mesh.

TABLE 2

| | Thickness (mm) | Areal Density (g/m²) | Burst Strength (N) | Elongation (%) | Peak Load (N) | Pore size μm) | Residual Monomer (wt %) | I.V. (dL/g) | Melt Temperature (° C.) |
|---|---|---|---|---|---|---|---|---|---|
| Avg | 0.57 | 232.97 | 490.07 | 73.40 | 456.68 | 82.13 | 0.63 | 1.70 | 171.98 |
| Min | 0.57 | 226.96 | 464.42 | 66.82 | 399.99 | 57.97 | 0.42 | 1.69 | 171.22 |
| Max | 0.59 | 243.18 | 521.59 | 76.22 | 523.43 | 116.01 | 0.80 | 1.72 | 172.62 |

Example 9

3D Printing of the Injection Molding Guide onto Barrier Mesh

A filament of injection molding guide material as identified in Table 3 was loaded into the 3D printer. The print bed of the printer was heated to about 100° C. after which the print bed was leveled. The print bed was then cooled to below about 50° C. and the barrier material (mesh) was placed on the print bed. The barrier material was secured to the print bed using adhesive tape. The temperature of the print bed was then raised to about 100° C. The injection molding guide was then printed onto the barrier material. Following printing, the printed material was kept on the print bed for a period of time to anneal the material. The print bed was then allowed to cool and once the print bed had cooled to a temperature at which the barrier material could be safely handled (<50° C.), the barrier material was removed from the print bed. Information about the barrier constructs that were printed is provided in Table 3 below:

| Construct # | Mesh Material | Injection molding guide material | Print bed Temp (° C.) | Print head temp (° C.) | Annealing time (min) | Injection molding guide shape |
|---|---|---|---|---|---|---|
| 1 | Lactoprene ® 8812 polymer | Lactoprene ® 8812 polymer | 100 | 220 | 30 | L-shape |
| 2 | Polyester (non-absorbable) | Lactoprene ® 8812 polymer | 100 | 220 | 30 | L-shape |
| 3 | Polyester (non-absorbable) | ABS | 100 | 240 | 30 | L-shape |
| 4 | Polypropylene (non-absorbable) | Polypropylene | 100 | 230 | 0 | L-shape |

Example 10

3D Printing of Injection Molding Guides

Lactoprene® 8812 polymer was used to 3D print an L-shaped injection molding guide onto lactide/TMC knitted barrier material. The knit pattern was a tricot based pattern that used a 2 ply/43 (86 total count) count yarn A filament of Lactoprene® 8812 polymer was loaded into the 3D printer. The print bed of the printer was heated to about 100° C. after which the print bed was leveled. The injection molding guide was then printed onto the print bed. Following printing, the printed material was kept on the print bed for a period of time to anneal the material. The print bed was then allowed to cool and once the print bed had cooled to a temperature at which the injection molding guides could be safely handled (<50° C.), the injection molding guide was removed from the print bed. This process was repeated several times, and the properties of the injection molding guides that were printed are detailed in Table 4 below, where I.D. refers to inner diameter and O.D. refers to outer diameter of the injection molding guides:

TABLE 4

|  | Mass (g) | I.D. (mm) | O.D. (mm) | Lower Thickness (mm) | Step Height (mm) | Upper Thickness (mm) |
|---|---|---|---|---|---|---|
| Average | 0.77 | 44.39 | 49.28 | 0.97 | 0.49 | 1.47 |
| Min | 0.74 | 43.27 | 48.89 | 0.88 | 0.39 | 1.36 |
| Max | 0.82 | 44.70 | 49.63 | 1.09 | 0.55 | 1.57 |

Example 11

Injection Molded Construct

A piece of mesh prepared as in Example 5 was cut to approximately the size of the mold. The mesh was inserted into the mold. The mold was closed and an L-shaped injection molding guide was over-molded onto the mesh using Lactoprene® 8812 polymer. The resulting mesh construct was removed from the mold and the excess mesh on the outer edge of the construct was trimmed off the construct.

Example 12

Sieving of Glycine

The glycine was sieved prior to incorporation into the silicone. A 200 Mesh sieve was added on top of a sieving collection pan. A 100 mesh sieve was then added to the top of the 200 Mesh sieve. About 600 g glycine was added to the 100 Mesh sieve. A cover was placed on the 100 Mesh sieve. The sieve combination was placed into a mechanical sieve shaker. The sieve shaker was run for 10 minutes. The cover and 100 Mesh sieve were removed and the glycine collected on the 200 Mesh sieve was placed in a plastic bag. The process was repeated until sufficient sieved glycine was obtained. The plastic bags were then heat sealed and stored.

Example 13

Sieving of Ferrous Gluconate

The ferrous gluconate was sieved prior to incorporation into the silicone. A 140 Mesh sieve was added on top of a sieving collection pan. A 100 mesh sieve was then added to the top of the 140 Mesh sieve. About 600 g ferrous gluconate was added to the 100 Mesh sieve. A cover was placed on the 100 Mesh sieve. The sieve combination was placed into a mechanical sieve shaker. The sieve shaker was run for 10 minutes. The cover and 100 Mesh sieve were removed and the ferrous gluconate collected on the 140 Mesh sieve was placed in a plastic bag. The process was repeated until sufficient sieved ferrous gluconate was obtained. The plastic bags were then heat sealed and stored.

Example 14

Milling and Micronizing of Polyglycolic Acid Powder

Polyglycolide polymer that comprised a terminal carboxylic acid group (inherent viscosity about 0.13 dL/g) was milled to a powder using a Thomas Model 4 Wiley Mill. The polyglycolide powder was then further micronized using a Fluid Energy Aljet Jet-O-Mizer™ micronizer (Model 0101, 2 mm screen) with a Schenck AccuRate® Tuf-Flex™ volumetric feeder (Model 102) was set up with a half pitch feeder screw for the feeder. The nitrogen pressure was adjusted until the delivery pressure shown on the gauges for the pusher and grinder nozzles each read about 120 psi. The polyglycolide polymer was poured into the feed hopper and the feed setting was adjusted to 2. The micronizer and the feeder was turned which allowed the polymer to pass into the micronizer and the polymer to be micronized. The output from the micronizer was collected in a plastic container. Once all the polymer has been micronized and collected, the collection container was closed and the instrument was turned off.

Example 15

A medical grade two-part platinum cured silicone (Silastic® Q7-4840 silicone) was used to prepare the silicone component of the ring. About 3 kg of the Silastic® Part A was added to the bowl of a Jaygo mixing unit. About 330 g ascorbic acid, 441 g ferrous gluconate, 184 g glycine and 184 g of a powdered polyglycolide polymer was added to the Silastic® Part A. The materials were mixed for approximately 35 minutes after which a vacuum was applied to the mixing bowl and the mixture was mixed for an additional 60 minutes. The mixing was turned off for 30 minutes to allow the mixture to degas. The mixture was then mixed slowly for an additional 20 minutes. The vacuum was released and the mixture was transferred to a plastic pail. The plastic pail was then sealed. This process was repeated using about 3 kg of Silastic® Part B.

Example 16

The ferrous gluconate and ascorbic acid loaded Silastic® Part A and Part B, from Example 15, were loaded into a liquid silicone rubber injection molding apparatus. The barrier material with a 3D printed injection molding guide was placed in a custom stainless-steel mold. The top part of the mold was closed to the bottom part of the mold and a clamp force was applied to the mold. The Silastic® Part A and Part B were mixed inline and injected into the mold. The Silastic® was cured at about 120° C. for about 2-3 minutes with a clamp pressure of about 180 kN. The mold was opened and the formed device was removed from the mold and was allowed to cool to room temperature.

Example 17

The ring (Example 16) was placed in a Tyvek pouch which was then heat sealed. The ring was sterilized using ethylene oxide (ETO). The sterile rings were then dried under vacuum for about 7 days. The ring in the Tyvek pouch was then placed in a labeled foil pouch which was heat sealed.

Example 18

The properties of completed contraceptive devices that had undergone ETO sterilization and final packaging were measured. The contraceptive devices comprised a lactide/TMC polymer knitted mesh with ferrous gluconate, ascorbic acid, glycine and a polyglycolide particles as part of the cured silicone ring. The devices comprised a lactide/TMC 3D printed injection molding guide that was attached to the mesh prior to injection molding the silicone ring component. The outer diameter of the contraceptive device and the inner diameter of the silicone ring component were measured using a caliper. Four measurements were made per ring, and three lots of rings were evaluated. The results are provided in Table 5.

TABLE 5

| No. of lots | 3 |
| --- | --- |
| Range of average O.D. (mm) per lot | 53.5 to 53.9 |
| Range of minimum O.D. (mm) per lot | 53.1 to 53.5 |
| Range of maximum O.D. (mm) per lot | 54.0 to 54.3 |

The mass of the devices were measured using a balance; see Table 6.

TABLE 6

| No. of lots | 3 |
| --- | --- |
| Range of average mass (g) per lot | 5.53 to 5.58 |
| Minimum mass (g) of rings | 5.48 |
| Maximum mass (g) of rings | 5.60 |

The pore size of a mesh is the measured distance between the knit intersticies. A microscope was setup with the objective lens set to 4×, the microscope's light source set at maximum and with an additional external light source focused on the middle of the microscope stage. The software system used (Motic Images plus 2.0) was calibrated using a calibration slide. The contraceptive device was placed on the microscope stage such that the barrier material was placed in the focal path of the microscope. After focusing the image, a 3664×2748 pixel image of the barrier material was captured using a digital camera connected to Motic Images plus 2.0 software. The accuracy was set to 0.01 μm. The pore size was measured as the short width distance between the knit intersticies of the top layer of the barrier material. This process was repeated until at least 10 measurements were made for each mesh within each lot. See Table 7.

TABLE 7

| No. of lots | 3 |
| --- | --- |
| Range of average pore size (μm) per lot | 108 to 119 |
| Minimum pore size (μm) of rings | 81 |
| Maximum pore size (μm) of rings | 161 |

The mesh-ring integrity test determines the force (N) resulting from the displacement of the mesh portion of the contraceptive device over a set distance while the silicone ring remains constrained using a ball burst strength apparatus. The contraceptive device is placed in a custom ball burst frame after which the top part of the frame was closed such that the silicone ring portion of the contraceptive device was tightly held in the frame. The ball attachment was attached to the load cell which was attached to the MTS mechanical tester. The ball attachment was lowered until it was position immediately above the barrier portion of the contraceptive device. The test was then started with the ball attachment being forced against the barrier component of the contraceptive device. The peak load was measured. See Table 8.

TABLE 8

| No. of lots | 3 |
| --- | --- |
| Range of average peak load (N) per lot | 440 to 529 |
| Minimum peak load (N) of rings | 329 |
| Maximum peak load (N) of rings | 563 |

The compressive deformation or bending force was measured for the contraceptive device. Two flat plates were attached to a MTS Synergie 200 mechanical tester. The contraceptive device was placed vertically on the bottom plate and then the top plate was lowered until the plate touches the device and holds the device in place. The load force observed should be less than 0.25N. The test is then started such that the top plate moves downwards at a rate of 1 mm/s for a total distance of 1 inch. The peak load force was measured for each ring in three lots of rings. See Table 9.

TABLE 9

| No. of lots | 3 |
|---|---|
| Range of average peak load force (N) per lot | 3.0 to 3.2 |
| Minimum peak load force (N) of rings | 2.2 |
| Maximum peak load force (N) of rings | 4.2 |

Example 19

Permittivity Testing

The permittivity of various knitted meshes, and constructs of knitted meshes with injection molded guides, were evaluated. In each case, the barrier material was a lactide/TMC copolymer knitted in a tricot pattern. Permittivity was tested using ASTM D 4491 using the constant head test. See Table 10.

TABLE 10

| Sample | Yarn | Average flow rate (gallons/min/square foot) |
|---|---|---|
| Mesh 1 | 2 ply/43 count | 115.6 |
| Mesh 2 | 2 ply/43 count | 131.2 |
| Mesh 3 | 2 ply/43 count | 129.7 |
| Mesh 4 | 2 ply/43 count | 152.5 |
| Mesh 5 | 1 ply/86 count | 148.9 |
| Construct 1 | 2 ply/43 count | 133.3 |
| Construct –2 | 2 ply/43 count | 127.5 |
| Construct –3 | 2 ply/43 count | 119.8 |
| Construct 4 | 2 ply/43 count | 183.3 |
| Construct 5 | 1 ply/86 count | 151.6 |

What is claimed is:

1. A contraceptive device comprising:

a polymeric ring, a porous barrier material and an injection molding guide, both of the injection molding guide and the porous barrier material at least partially embedded within the polymeric ring, wherein the injection molding guide comprises a plurality of planar surfaces, wherein the injection molding guide has a corner formed by two planar surfaces intersecting at an angle, and wherein the injection molding guide has a cross-section with a L-shape, a T-shape, an off-set T-shape, a U-shape, a V-shape, a partial V-shape, or an irregular shape.

2. The contraceptive device of claim 1 wherein the barrier material is a mesh.

3. The contraceptive device of claim 1 wherein the barrier material is fibrous.

4. The contraceptive device of claim 1 wherein the injection molding guide is symmetrical.

5. The contraceptive device of claim 1 wherein the angle is between a 45 degree angle and a 135 degree angle.

6. The contraceptive device of claim 1 wherein the injection molding guide is affixed to the porous barrier material.

7. The contraceptive device of claim 1 wherein the injection molding guide is biodegradable.

8. The contraceptive device of claim 1 wherein the injection molding guide extends into the porous barrier material.

9. The contraceptive device of claim 1 wherein the polymeric ring comprises an elastomeric polymer.

10. The contraceptive device of claim 1 wherein the polymeric ring encircles the porous barrier material.

11. The contraceptive device of claim 1 further comprising a biologically active agent located within the polymeric ring.

12. The contraceptive device of claim 1 wherein the angle is about 90 degrees.

13. The contraceptive device of claim 1, wherein the injection molding guide has a cross-section with a L-shape, a T-shape, an off-set T-shape, a U-shape, a V-shape, a partial V-shape.

14. The contraceptive device of claim 1, wherein the injection molding guide has an L-shaped cross-section.

15. A kit comprising the contraceptive device of claim 1, the kit further comprising at least one of a lubricant, a spermicidal gel, a spermicidal film, a contraceptive gel and an applicator.

* * * * *